United States Patent
Heuer et al.

(10) Patent No.: US 7,863,403 B2
(45) Date of Patent: Jan. 4, 2011

(54) PROCESS FOR THE PREPARATION OF POLYCARBONATES AND DIARYL CARBONATE

(75) Inventors: Helmut-Werner Heuer, Krefeld (DE); Pieter Ooms, Krefeld (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/370,182

(22) Filed: Feb. 12, 2009

(65) Prior Publication Data

US 2009/0240021 A1 Sep. 24, 2009

(30) Foreign Application Priority Data

Feb. 13, 2008 (DE) ........................ 10 2008 008 841
Aug. 16, 2008 (DE) ........................ 10 2008 038 031

(51) Int. Cl.
*C08G 64/00* (2006.01)
*C08G 63/02* (2006.01)

(52) U.S. Cl. ........................ 528/196; 422/135; 528/198

(58) Field of Classification Search .................. 422/135; 528/196, 198

See application file for complete search history.

(56) References Cited

U.S. PATENT DOCUMENTS

| | | | |
|---|---|---|---|
| 2,964,794 A | 12/1960 | Peilstöcker et al. | |
| 3,986,269 A | 10/1976 | Hancock | |
| 4,016,190 A | 4/1977 | Böckmann et al. | |
| 4,423,207 A | 12/1983 | Flock et al. | |
| 4,851,571 A | 7/1989 | Sauer et al. | |
| 4,980,105 A | 12/1990 | Schmidt et al. | |
| 6,340,736 B1 | 1/2002 | Coenen et al. | |
| 6,531,623 B2 * | 3/2003 | Chrisochoou et al. | 558/274 |
| 6,534,094 B2 * | 3/2003 | Moyano et al. | 424/491 |
| 6,613,868 B2 | 9/2003 | Kauth et al. | |
| 2004/0158026 A1 | 8/2004 | Kauth et al. | |

FOREIGN PATENT DOCUMENTS

| | | |
|---|---|---|
| BE | 866991 | 11/1978 |
| DE | 1137167 | 9/1962 |
| DE | 2053876 | 5/1972 |
| DE | 2701173 A1 | 7/1978 |
| DE | 3332065 A1 | 3/1985 |
| DE | 3429960 A1 | 2/1986 |
| DE | 3717057 A1 | 12/1988 |
| DE | 4220239 C2 | 12/1993 |
| EP | 003996 B1 | 9/1979 |
| EP | 0070529 A1 | 1/1983 |
| EP | 0089801 A1 | 9/1983 |
| EP | 0256003 | 2/1988 |
| EP | 0267025 A1 | 5/1988 |
| EP | 0269324 A3 | 6/1988 |
| EP | 0411510 A3 | 2/1991 |
| EP | 0460450 A2 | 12/1991 |
| EP | 0517044 A3 | 12/1992 |
| EP | 0520272 A2 | 12/1992 |
| EP | 0634445 B1 | 1/1995 |
| EP | 0784048 B1 | 7/1997 |
| EP | 1200359 B1 | 5/2002 |
| EP | 1216981 A3 | 6/2002 |
| EP | 1216982 A3 | 6/2002 |
| EP | 1219589 B1 | 7/2002 |
| EP | 1249463 A3 | 10/2002 |
| WO | WO-03/070639 A1 | 8/2003 |

* cited by examiner

*Primary Examiner*—Terressa M Boykin
(74) *Attorney, Agent, or Firm*—Connolly Bove Lodge & Hutz LLP

(57) ABSTRACT

The present invention relates to a process for the continuous preparation of polycarbonates or diaryl carbonates by the method of the phase boundary process, in which both the mixing of the organic and aqueous phase and the upstream oligomerization step or aryl chloroformate and/or diaryl carbonate preparation step are effected in a special pump.

19 Claims, 6 Drawing Sheets

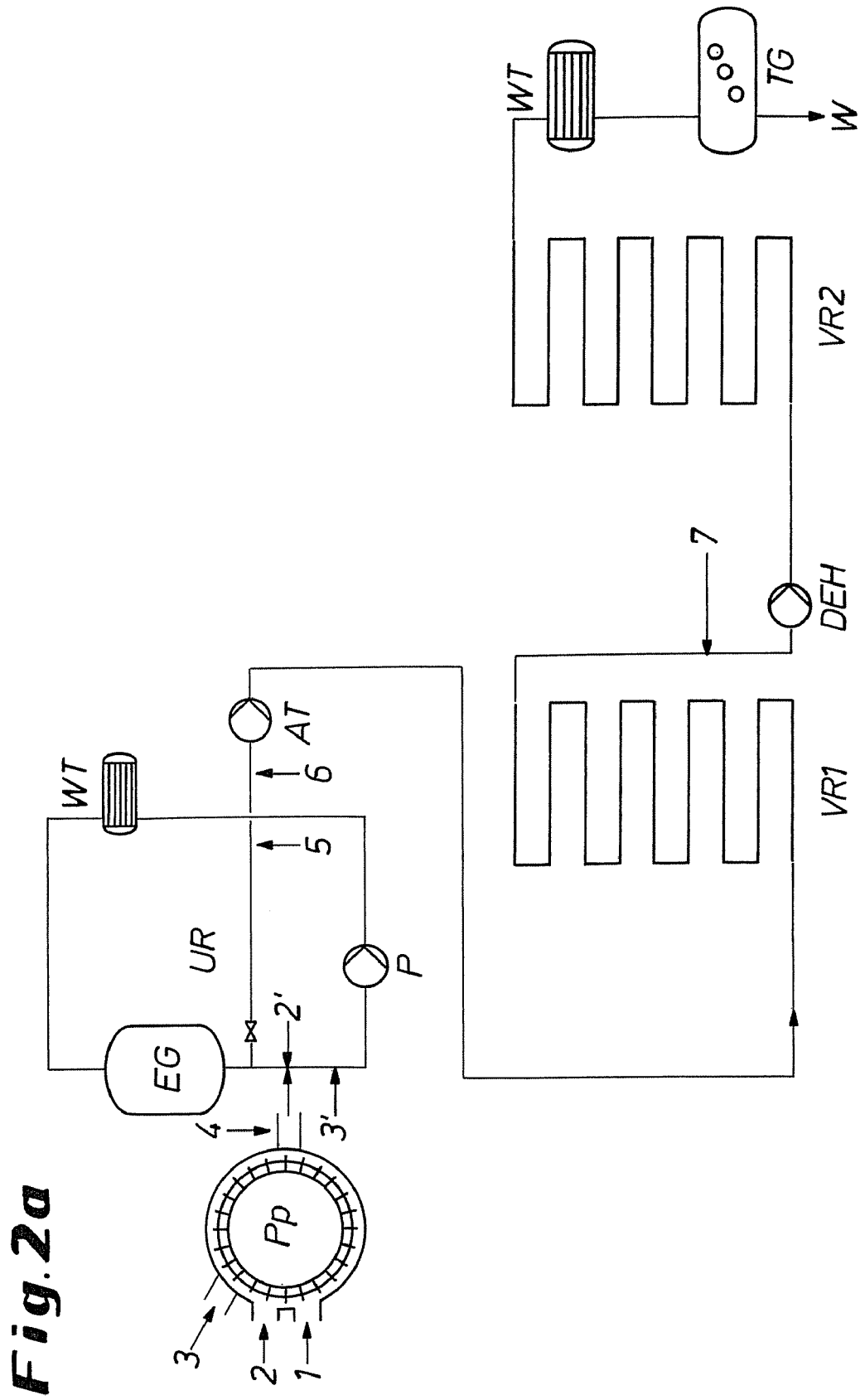

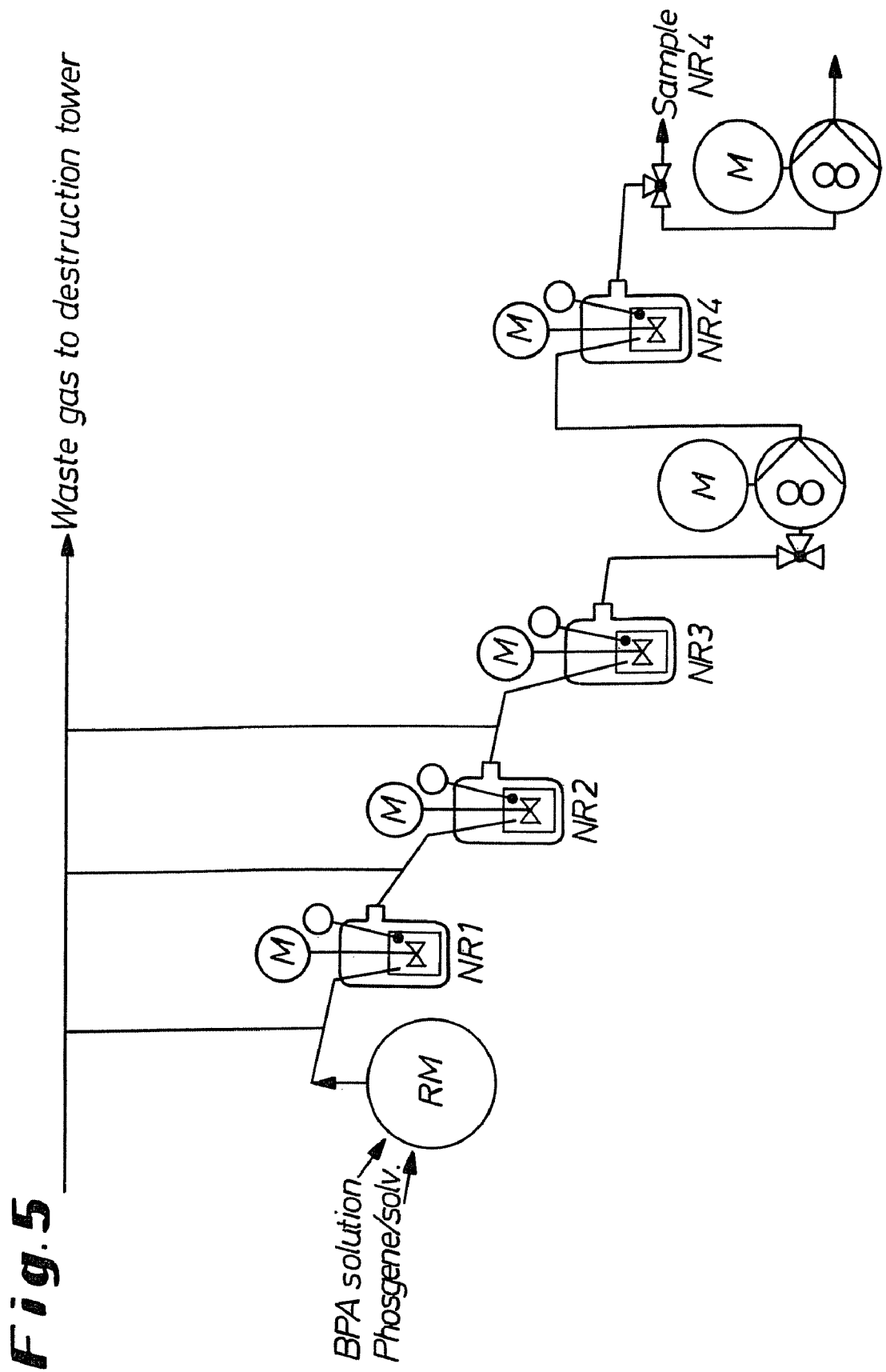

PROCESS FOR THE PREPARATION OF POLYCARBONATES AND DIARYL CARBONATE

RELATED APPLICATIONS

This application claims benefit to German Patent Application Nos. 10 2008 008 841.2, filed Feb. 13, 2008, and 10 2008 038 031.8, filed Aug. 16, 2008, which are incorporated herein by reference in their entireties for all useful purposes.

BACKGROUND OF THE INVENTION

The present invention relates to a process for the continuous preparation of polycarbonates and diaryl carbonates by the method of the phase boundary process in which both the mixing of the organic and aqueous phase and the upstream oligomerization step or the formation of the chloroformate of the monoaryl compound are effected in a special pump.

The polycarbonate preparation by the phase boundary process has already been described by Schnell, "Chemistry and Physics of Polycarbonates", Polymer Reviews, Volume 9, Interscience Publishers, New York, London, Sydney 1964, pages 33-70; D. C. Prevorsek, B. T. Debona and Y. Kesten, Corporate Research Center, Allied Chemical Corporation, Morristown, N.J. 07960: "Synthesis of Poly(ester Carbonate) Copolymers" in Journal of Polymer Science, Polymer Chemistry Edition, Vol. 18, (1980)"; pages 75-90, D. Freitag, U. Grigo, P. R. Müller, N. Nouvertne', BAYER AG, "Polycarbonates" in Encyclopedia of Polymer Science and Engineering, Volume 11, Second Edition, 1988, pages 651-692, and finally by Dres. U. Grigo, K. Kircher and P. R-Müller, "Polycarbonate [Polycarbonates]" in Becker/Braun, Kunststoff-Handbuch [Plastics Handbook], volume 3/1, Polycarbonate, Polyacetale, Polyester, Celluloseester [Polycarbonates, Polyacetals, Polyesters, Cellulose Esters], Carl Hanser Verlag Munich, Vienna 1992, pages 118-145.

Furthermore, the phase boundary process for the preparation of polycarbonate is also described in EP-A 0 517 044 or EP-A 520 272:

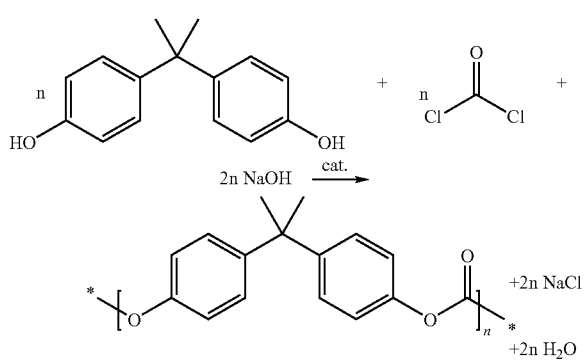

For the preparation of polycarbonate by the phase boundary process, the phosgenation of a disodium salt of a bisphenol or a mixture of different bisphenols, initially introduced into aqueous alkaline solution or suspension, is effected in the presence of an inert organic solvent or solvent mixture which forms a second organic phase in addition to the aqueous phase. The resulting oligocarbonates mainly present in the organic phase are condensed with the aid of suitable catalysts to give high molecular weight polycarbonates dissolved in the organic phase, it being possible to control the molecular weight by suitable chain terminators (monofunctional phenols). The organic phase is finally separated off and the polycarbonate is isolated therefrom by various working-up steps.

The polycarbonate synthesis and the diaryl carbonate synthesis can be carried out continuously or batchwise. The reaction can therefore be effected in stirred tanks, tubular reactors, pumped circulation reactors or stirred tank cascades or combinations thereof, it being ensured by use of the above-mentioned mixing members that aqueous and organic phase separate as far as possible only when the synthesis mixture has completely reacted, i.e. no longer contains any hydrolyzable chlorine from phosgene or chlorocarbonic acid esters.

The first step for the synthesis of the oligocarbonates is carried out according to the prior art, for example in a pumped circulation reactor; cf. for example EP 1 249 463 A1, US 2004/0158026 A1, U.S. Pat. No. 6,613,868 B2. In the pumped circulation reactor, the mixing of the introduced phosgene with likewise introduced disodium salt of a bisphenol (or of a mixture of different bisphenols) and the first oligomerization steps are effected. Resulting chloroformate groups react with terminal phenolate groups present to give growing oligomers which contain different terminal groups (phenolate or chloroformate or species mixed from the two). A certain proportion of bisphenol introduced is still present in unreacted form in the mixture. It is true that the pumped circulation reactor has advantages in that metering and concentration variations cannot continue unabated to the end product but rather an equilibrium of variations is achieved by back-mixing at a set circulation ratio for feed or discharge of the reaction mixture. However, there is a significant disadvantage in that relatively broad molecular weight distributions result for parameter settings which are advantageous on the industrial scale. A further disadvantage is that pumped circulation reactors are relatively bulky assemblies.

The preparation of diaryl carbonates (such as, for example, diphenyl carbonate) is usually effected by a continuous process, by preparation of phosgene and subsequent reaction of monophenols and phosgene in an inert solvent in the presence of alkali and a nitrogen catalyst at the boundary.

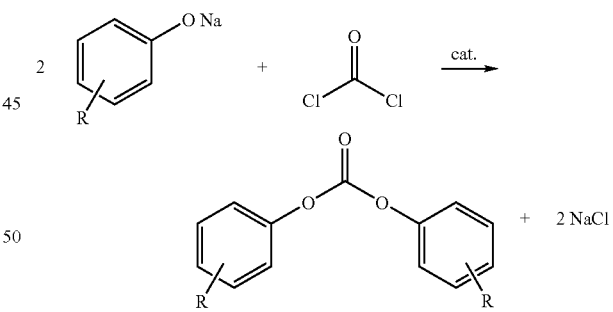

The preparation of diaryl carbonates, for example by the phase boundary process, is described in principle in the literature, cf. for example in Chemistry and Physics of Polycarbonates, Polymer Reviews, H. Schnell, Vol. 9, John Wiley and Sons, Inc. (1964), pages 50/51.

The laid-open application U.S. Pat. No. 4,016,190 describes a preparation process for diaryl carbonates which is operated at temperatures above 65° C. In this process, the pH is initially set low (pH=8 to 9) and then higher (pH=10 to 11).

Optimizations of the process by improvement of the mixing and maintenance of a narrow temperature and pH profile as well as isolation of the product are described in EP1219589 A1, EP1216981 A2, EP1216982 A2 and EP784048 A1.

For the preparation of diaryl carbonate by the phase boundary process, the phosgenation of an initially introduced sodium salt of a monophenol or of a mixture of different monophenols, in an aqueous alkaline solution or suspension, is effected in the presence of an inert organic solvent or solvent mixture which, in addition to the aqueous phase, forms a second organic phase. The resulting aryl chloroformates present mainly in the organic phase are converted with the aid of suitable catalysts to diaryl carbonates, dissolved in the organic phase. The organic phase is finally separated off and the diaryl carbonate is isolated therefrom by various work-up steps.

According to the prior art, the first step for the synthesis of the aryl chloroformates and/or diaryl carbonates is carried out, for example, in a pumped-circulation reactor; cf. for example EP 1 249 463 A1, US 2004/0158026 A1, U.S. Pat. No. 6,613,868 B2. In the pumped-circulation reactor, the mixing of the introduced phosgene with likewise introduced sodium salt of a monophenol (or of a mixture of different monophenols) to give aryl chloroformates and/or diaryl carbonates is effected. A certain proportion of the monophenol introduced is still present in unreacted form in the mixture. It is true that the pumped-circulation reactor has advantages in that metering or concentration variations cannot pass through undamped to the end product but rather an equilibration of variations is achieved by back-mixing at set pumped circulation ratio to feed or discharge of the reaction mixture. However, there is a significant disadvantage in that, for parameter settings advantageous in industry, there is still considerable incompletely reacted proportions of aryl chloroformates in the product composition. A further disadvantage is that pumped-circulation reactors are relatively bulky assemblies.

In these known processes, however, the high residual phenol value in the wastewater of these processes presents considerable disadvantages. Phenols can pollute the environment and cause increased wastewater problems for the wastewater treatment plants and necessitate complicated purification operations.

Thus, WO 03/070639 A1 describes removal of the organic impurities in the wastewater by extraction with methylene chloride.

Usually, the sodium chloride-containing solution is freed from solvents and organic residues and then has to be disposed of.

However, it is also known that, according to EP 1200359 B1 (WO2000078682 A1) or U.S. Pat. No. 6,340,736, the purification of the sodium chloride-containing wastewaters can be effected by ozonolysis and is then suitable for use in the sodium chloride electrolysis. A disadvantage of the ozonolysis is that this process is very expensive.

There was therefore a need for a continuous phase boundary process for the preparation of polycarbonate or diaryl carbonate, by means of which the pollution of the wastewater resulting from this process with diphenol or monophenol can be further reduced. Furthermore, it would be desirable if polycarbonates having narrower molecular weight distribution were obtained in such a process without it being possible, for example, for concentration variations to continue unabated to the end product (no plug flow behaviour). In the preparation of diaryl carbonates as well, this process prevents substantially unabated concentration variations of the aryl chloroformate up to the end product.

Surprisingly, it was found that a significant reduction in the diphenol or monophenol pollution of the wastewater can be achieved if both the mixing of the organic and aqueous phase and the upstream oligomerization step or the upstream chloroformic acid formation are effected in a special pump by the phase boundary process for the preparation of polycarbonates or diaryl carbonates. Advantageously, in this process too concentration variations do not continue unabated to the end product so that the process according to the invention retains advantages of the known process according to the prior art which eliminates disadvantages thereof. It is known that an increased diphenol and/or monophenol pollution of the wastewater requires, as a countermeasure, an increase in the phosgene and sodium hydroxide addition in order to complete the conversion of the diphenol or monophenol. Owing to the substantially reduced diphenol and/or monophenol pollution of the wastewater in the process according to the invention, it is therefore also possible to avoid such an increase in the phosgene and sodium hydroxide addition. This is advantageous, inter alia, from an economic point of view. Furthermore, the amount of aryl chloroformate decreases due to the more efficient reaction in the preparation of polycarbonates and diaryl carbonates, which requires a lower amount of amine catalyst and thus leads to a reduction in the urethane by-products.

EMBODIMENTS OF THE INVENTION

An embodiment of the present invention is a process for continuously preparing a polycarbonate or a copolycarbonate or a diaryl carbonate by the phase boundary process from a diphenol or a monophenol, phosgene and a catalyst, optionally in the presence of at least one chain terminator and/or branching agent, comprising (a) continuously mixing of an organic phase and an aqueous phase, said organic phase comprising a solvent suitable for said polycarbonate or copolycarbonate or diaryl carbonate and phosgene and said aqueous phase comprising said a diphenol or a monophenol, water, and alkali solution;

(b) reacting said diphenol or monophenol and said phosgene in the presence of a catalyst to give a polycarbonate or a copolycarbonate or an aryl chloroformate or a diaryl carbonate or a mixture of an aryl chloroformate and a diaryl carbonate; and (c) reacting said polycarbonate or copolycarbonate or aryl chloroformate or diaryl carbonate or mixture of aryl chloroformate and diaryl carbonate in a reactor with additional alkali solution and optionally a chain terminator and optionally a further catalyst;

wherein said continuous mixing in (a) and said reaction in (b) are effected in a pump, wherein said pump operates according to the stator-rotor principle;

is thermostatable; and comprises an entrance for said organic phase and an entrance for said aqueous phase and optionally comprises entrances for a catalyst a chain terminator, a branching agent, and/or additional alkali solution and at least one exit for said polycarbonate or copolycarbonate or aryl chloroformate or diaryl carbonate or mixture of aryl chloroformate and diaryl carbonate.

Another embodiment of the present invention is the above process, wherein a further catalyst is used in (c).

Another embodiment of the present invention is the above process, wherein said pump comprises entrances for additional alkali solution and at least one exit said polycarbonate or copolycarbonate or aryl chloroformate or diaryl carbonate or mixture of aryl chloroformate and diaryl carbonate.

Another embodiment of the present invention is the above process, wherein said pump has one or more rotors.

Another embodiment of the present invention is the above process, wherein said pump is thermostatable to a temperature of from 5° C. to 100° C.

Another embodiment of the present invention is the above process, wherein said pump is thermostatable to a temperature of from 15° C. to 80° C.

Another embodiment of the present invention is the above process, wherein said pump is thermostatable to a temperature of from 25° C. to 65° C.

Another embodiment of the present invention is the above process, wherein said diphenol is of formula

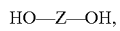

wherein Z is a divalent organic radical having 6 to 30 carbon atoms and which contains one or more aromatic groups.

Another embodiment of the present invention is the above process, wherein said diphenol is hydroquinone, resorcinol, dihydroxybiphenyls, bis(hydroxyphenyl)alkanes, bis(hydroxyphenyl)cycloalkanes, bis(hydroxyphenyl)sulphides, bis(hydroxyphenyl)ethers, bis(hydroxyphenyl)ketones, bis (hydroxyphenyl)sulphones, bis(hydroxyphenyl)sulphoxides, α,α'-bis(hydroxyphenyl)diisopropylbenzenes, bis(hydroxyphenyl)phthalimidines or the compounds thereof which are alkylated, alkylated on the nucleus, or halogenated on the nucleus.

Another embodiment of the present invention is the above process, wherein said diphenol is 4,4'-dihydroxybiphenyl, 2,2-bis(4-hydroxyphenyl)-1-phenylpropane, 1,1-bis(4-hydroxyphenyl)phenylethane, 2,2-bis(4-hydroxyphenyl)propane (bisphenol A (BPA)), 2,4-bis(4-hydroxyphenyl)-2-methylbutane, 1,3-bis[2-(4-hydroxyphenyl)-2-propyl]benzene (bisphenol M), 2,2-bis(3-methyl-4-hydroxyphenyl)propane, bis(3,5-dimethyl-4-hydroxyphenyl)methane, 2,2-bis(3,5-dimethyl-4-hydroxyphenyl)propane, bis(3,5-dimethyl-4-hydroxyphenyl)sulphone, 2,4-bis(3,5-dimethyl-4-hydroxyphenyl)-2-methylbutane, 1,3-bis[2-(3,5-dimethyl-4-hydroxyphenyl)-2-propyl]benzene, 2-hydroxycarbyl-3,3-bis (4-hydroxyphenyl)-phthalimidine, 3,3-bis(4-hydroxyphenyl)-1-phenyl-1H-indol-2-one, 2,2-bis(4-hydroxy-phenyl)-1-phenyl-1H-indol-2-one, 3,3-bis(4-hydroxyphenyl)-1-methyl-1H-indol-2-one, 2,2-bis(4-hydroxyphenyl)-1-methyl-1H-indol-2-one, 3,3-bis(4-hydroxyphenyl)-N-methylphthalimidine, 3,3-bis(4-hydroxyphenyl)-N-phenylphthalimidine or 1,1-bis-(4-hydroxyphenyl)-3,3,5-trimethylcyclohexane (bisphenol TMC).

Another embodiment of the present invention is the above process, wherein said monophenol is of formula (I):

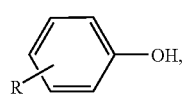

wherein R is hydrogen, halogen, or a branched or straight-chain $C_1$- to $C_9$-alkyl radical or alkoxycarbonyl radical.

Another embodiment of the present invention is the above process, wherein said monophenol is phenol, cresols, p-tert-butylphenol, p-cumylphenol, p-n-octylphenol, p-isooctylphenol, p-n-nonylphenol, p-isononylphenol, p-chlorophenol, 2,4-dichlorophenol, p-bromophenol, 2,4,6-tribromophenol, methyl salicylate, or a mixture thereof.

Another embodiment of the present invention is the above process, wherein said pump in (a) and/or (b) is a centrifugal pump.

Another embodiment of the present invention is the above process, wherein said centrifugal pump is a peripheral wheel pump.

Another embodiment of the present invention is the above process, wherein said pump is designed according to the one-chamber or multichamber principle.

Yet another embodiment of the present invention is a pump for continuously preparing polycarbonate or diaryl carbonate by the phase boundary process, wherein said pump
  operates according to the stator-rotor principle;
  is thermostatable; and
  comprises at least one entrance for an organic phase and at least one entrance for an aqueous phase.

Another embodiment of the present invention is the above pump, wherein said pump further comprises entrances for a chain terminator, a branching agent, and/or an alkali solution, and a catalyst, and at least one exit for polycarbonate or copolycarbonate or aryl chloroformate or diaryl carbonate or mixture of aryl chloroformate and diaryl carbonate.

Another embodiment of the present invention is the above pump, wherein said pump continually effects (1) the mixing of said organic phase and said aqueous phase, wherein said organic phase comprises a solvent suitable for said polycarbonate or copolycarbonate or diaryl carbonate and phosgene and said aqueous phase comprises a diphenol or a monophenol, water, and alkali solution, and (2) the reaction of said diphenol or said monophenol and phosgene to give a polycarbonate or a copolycarbonate or an aryl chloroformate or a diaryl carbonate or a mixture of aryl chloroformate and diaryl carbonate.

Another embodiment of the present invention is the above pump, wherein said pump is a centrifugal pump.

Another embodiment of the present invention is the above pump, wherein said centrifugal pump is a peripheral wheel pump.

BRIEF DESCRIPTION OF THE DRAWINGS

FIG. 2a is a schematic setup for the preparation of polycarbonate or diaryl carbonate by the phase boundary process using a peripheral wheel pump with downstream pump circulation reactor

FIG. 5 is an experimental setup using a peripheral wheel pump according to the invention.

DESCRIPTION OF THE INVENTION

Figure 1:
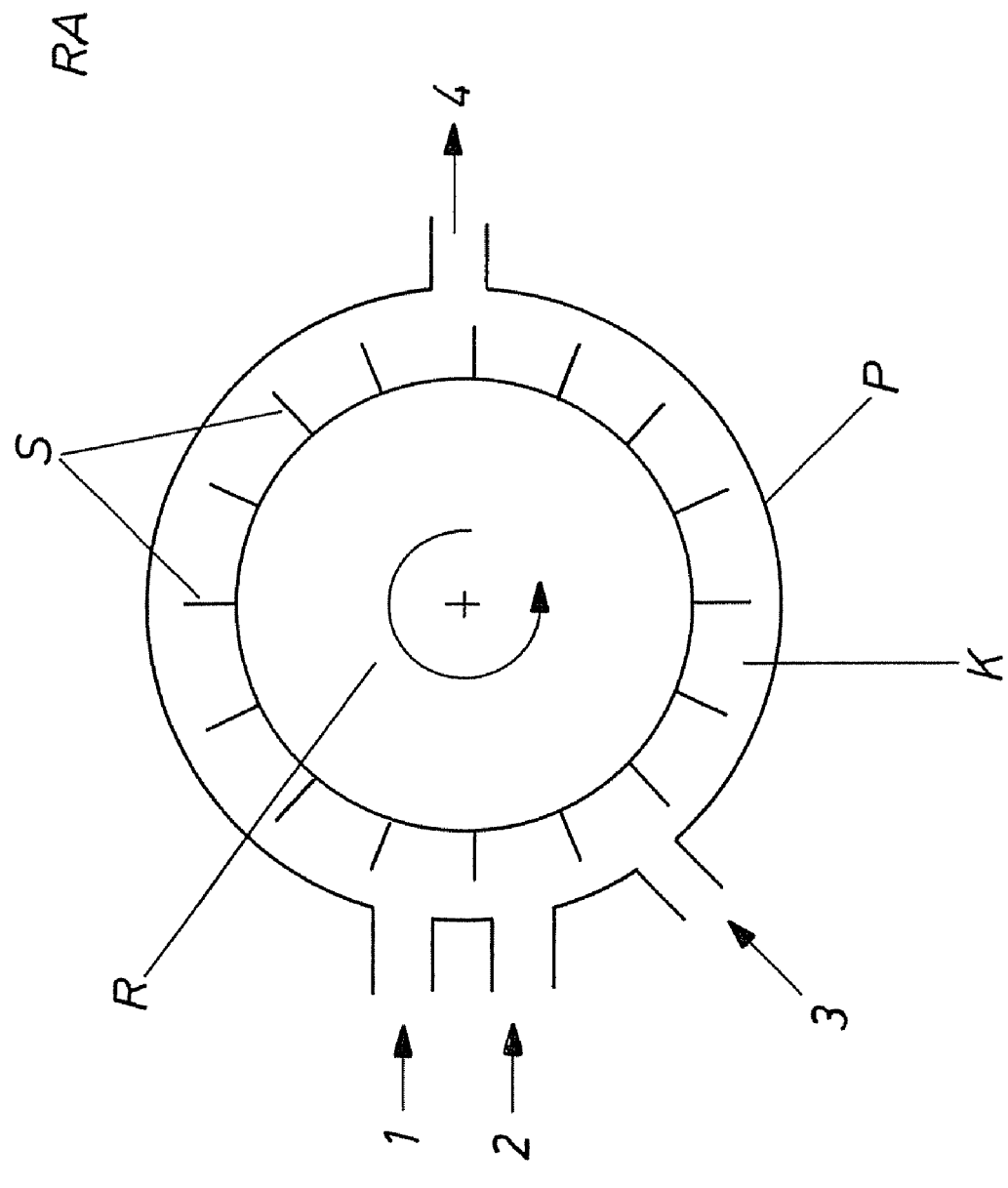
FIG. 1 is a schematic diagram of the principal of the peripheral wheel pump having a rotating internal apparatus.

The present invention therefore relates to a process for the continuous preparation of polycarbonates or copolycarbonates or diaryl carbonates by the phase boundary process from at least one diphenol or monophenol, phosgene and at least one catalyst, optionally in the presence of at least one chain terminator and/or branching agent, characterized in that
(a) a mixture of the organic and aqueous phase is produced continuously, the organic phase containing at least one solvent suitable for the polycarbonate or diaryl carbonate and all or some of the phosgene and the aqueous phase containing the diphenol(s) or monophenol(s), water and alkali solution, (b) a reaction of the diphenol(s) or monophenol(s) and phosgene takes place to give oligocarbonates or to give aryl chloroformates or diaryl carbonates or a mixture of aryl chloroformates and diaryl carbonates, (c) the oligocarbonates or aryl chloroformates and/or diaryl carbonates are then reacted in at least one reactor with addition of further alkali solution, optionally chain terminator(s) and optionally at least one further catalyst, characterized in that the continuous mixing of the organic and aqueous phase under (a) and the reaction to give oligocarbonates or aryl chloroformates and/or diaryl carbonates under (b) are effected in one or more pump(s) which operates or operate according to the stator-rotor principle is or are thermostatable and has or have in each case at least one entrance for the organic and the aqueous phase and optionally further entrances for a catalyst, chain terminator, branching agent and/or additionally alkali solution and at least one exit for the oligocarbonate-containing or aryl chloroformate/diaryl carbonate mixture.

In the process according to the invention for the preparation of polycarbonate or diaryl carbonate, at least some of the alkali chloride-containing solution which occurs in the process can be recycled to a downstream alkali chloride electrolysis.

The pump(s) used according to the invention are preferably designed according to the one-chamber or multichamber principle.

The organic phase may already contain some or all of the required phosgene before the mixing with the aqueous phase. Preferably, the organic phase already contains the total amount of required phosgene, including the phosgene excess used, before the mixing.

The introduction of the phosgene into the organic phase in the preparation of polycarbonate can be effected in gaseous or liquid form. The excess of phosgene used, based on the sum of the diphenols used, is preferably between 3 and 100 mol %, particularly preferably between 5 and 50 mol %.

The introduction of the phosgene into the organic phase in the preparation of diaryl carbonate can be effected in gaseous or liquid form. The excess of phosgene used, based on the sum of the monophenols used, is preferably between 1 and 100 mol %, particularly preferably between 2 and 50 mol %.

The pH of the aqueous phase should be kept in the alkaline range, preferably between 8.5 and 12, while optionally metering further alkali solution once or several times during and after the phosgene metering, while it should be 10 to 14 after the addition of catalysts.

The phosgene metering is effected before the mixing with the aqueous phase, completely or partly directly into the organic phase. Any portions of phosgene can also be metered into the aqueous phase before the mixing with the aqueous phase or into the resulting emulsion after the mixing with the aqueous phase. Furthermore, can the phosgene either completely or partly be metered into a recycled part-stream of the synthesis mixture of both phases, this part-stream preferably being recycled before the addition of catalysts. Particularly preferably, the complete phosgene metering is effected before the mixing with the aqueous phase, directly into the organic phase. In all these embodiments, the pH ranges described above should be maintained, if appropriate by metering of further sodium hydroxide solution or alkali solution once or several times or correspondingly metering further diphenyl (ate) solution or monophenol(ate) solution. Likewise, the temperature range must be maintained, if appropriate by cooling or dilution.

The synthesis of polycarbonates from dihydroxydiarylalkanes (diphenols) or of diaryl carbonates from monophenols and phosgene in an alkali medium is an exothermic reaction and is carried out in a temperature range of −5° C. to 100° C., preferably of 15° C. to 80° C., very particularly preferably of 25 to 65° C.

It is therefore necessary for the pump(s) used according to the invention for the mixing and the upstream oligomerization step or chloroformate formation to be thermostatable to a temperature of −5° C. to 100° C., preferably of 15° C. to 80° C., particularly preferably of 25° C. to 65° C.

Depending on solvent or solvent mixture, atmospheric pressure or superatmospheric pressure can be employed. The pump(s) used according to the invention can be designed for system pressures up to 350 bar and 450° C. They are therefore suitable for use in a broad process window.

In the phase boundary process, preferably pressure ranges of 1 to 50 bar, particularly preferably ranges of 1 to 10 bar, are employed.

The organic phase may contain one solvent or mixtures of a plurality of solvents. Suitable solvents are aromatic and/or aliphatic chlorinated hydrocarbons, preferably dichloromethane, trichloroethylene, 1,1,1-trichloroethane, 1,1,2-trichloroethane and chlorobenzene and mixtures thereof. However, it is also possible to use aromatic hydrocarbons, such as benzene, toluene, m-/p-/o-xylene, or aromatic ethers, such as anisole, alone, as a mixture or additionally or as a mixture with chlorinated hydrocarbons; dichloromethane and chlorobenzene and mixtures thereof are preferred. Another embodiment of the synthesis uses solvents which do not dissolve but only partly swell polycarbonate. It is therefore also possible to use nonsolvents for polycarbonate in combination with solvents. In this case, it is also possible to use, as solvents, solvents soluble in the aqueous phase, such as tetrahydrofuran, 1,3- or 1,4-dioxane or 1,3-dioxolane, if the solvent partner forms the second organic phase.

Suitable diphenols are those of the general formula

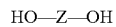

HO—Z—OH in which Z is a divalent organic radical having 6 to 30 carbon atoms, which contains one or more aromatic groups. Examples of such compounds which can be used in the process according to the invention are dihydroxydiarylalkanes, such as hydroquinone, resorcinol, dihydroxybiphenyl, bis(hydroxyphenyl)alkanes, bis(hydroxyphenyl)cycloalkanes, bis(hydroxyphenyl)sulphides, bis(hydroxyphenyl)ethers, bis(hydroxyphenyl)ketones, bis(hydroxyphenyl)sulphones, bis(hydroxyphenyl)sulphoxides, α,α'-bis(hydroxyphenyl)diisopropylbenzenes, bis(hydroxyphenyl)phthalimidines and compounds thereof which are alkylated, alkylated on the nucleus and halogenated on the nucleus.

Preferred diphenols are 4,4'-dihydroxybiphenyl, 2,2-bis(4-hydroxyphenyl)-1-phenylpropane, 1,1-bis(4-hydroxyphenyl)phenylethane, 2,2-bis(4-hydroxyphenyl)propane (bisphenol A (BPA)), 2,4-bis(4-hydroxyphenyl)-2-methylbutane, 1,3-bis[2-(4-hydroxyphenyl)-2-propyl]benzene (bisphenol M), 2,2-bis(3-methyl-4-hydroxyphenyl)propane, bis(3,5-dimethyl-4-hydroxyphenyl)-methane, 2,2-bis(3,5-dimethyl-4-hydroxyphenyl)propane, bis(3,5-dimethyl-4-hydroxyphenyl)sulphone, 2,4-bis(3,5-dimethyl-4-hydroxyphenyl)-2-methylbutane, 1,3-bis[2-(3,5-dimethyl-4-hydroxyphenyl)-2-propyl]benzene, 1,1-bis(4-hydroxyphenyl)cyclohexane, 2-hydrocarbyl-3,3-bis(4- hydroxyaryl)phthalimidines, 3,3-bis(4-hydroxyaryl)-1-aryl-1H-indol-2-one, 2,2-bis(4-hydroxyaryl)-1-aryl-1H-indol-2-one and 1,1-bis(4-hydroxyphenyl)-3,3,5-trimethylcyclohexane (bisphenol TMC).

Particularly preferred diphenols are 4,4'-dihydroxybiphenyl, 1,1-bis(4-hydroxyphenyl)-phenylethane, 2,2-bis(4-hydroxyphenyl)propane (bisphenol A (BPA)), 2,2-bis(3,5-dimethyl-4-hydroxyphenyl)propane, 1,1-bis(4-hydroxyphenyl)cyclohexane, 2-hydroxycarbyl-3,3-bis(4-hydroxyphenyl)phthalimidine, 3,3-bis(4-hydroxyphenyl)-1-phenyl-1H-indol-2-one, 2,2-bis(4-hydroxyphenyl)-1-phenyl-1H-indol-2-one, 3,3-bis(4-hydroxyphenyl)-1-methyl-1H-indol-2-one, 2,2-bis(4-hydroxyphenyl)-1-methyl-1H-indol-2-one, 3,3-bis(4-hydroxyphenyl)-N-methyl-phthalimidine, 3,3-bis(4-hydroxyphenyl)-N-phenyl-phthalimidine and 1,1-bis(4-hydroxyphenyl)-3,3,5-trimethylcyclohexane (bisphenol TMC).

These and further suitable diphenols are described, for example, in U.S. Pat. No. 2,999,835, U.S. Pat. No. 3,148,172, U.S. Pat. No. 2,991,273, U.S. Pat. No. 3,271,367, U.S. Pat. No. 4,982,014 and U.S. Pat. No. 2,999,846, in the German laid-open patent applications DE-A 1 570 703, DE-A 2 063 050, DE-A 2 036 052, DE-A 2 211 956 and DE-A 3 832 396, the French patent FR-A 1 561 518, in the monograph by H. Schnell, Chemistry and Physics of Polycarbonates, Interscience Publishers, New York 1964, page 28 et seq.; page 102 et seq., and by D. G. Legrand, J. T. Bendler, Handbook of Polycarbonate Science and Technology, Marcel Dekker New York 2000, page 72 et seq.

In the case of the preparation according to the invention of homopolycarbonates, only one diphenol is used; in the case of the preparation according to the invention of copolycarbonates, a plurality of diphenols is used, it of course being possible for the diphenols used, as well as all other chemicals and auxiliaries added to the synthesis, to be contaminated with the impurities originating from their own synthesis, handling and storage, although it is desirable to work with raw materials which are as pure as possible.

Particularly suitable monophenols for use in the novel process are phenols of the formula (I)

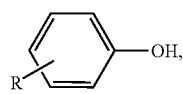

(I)

in which
R is hydrogen, halogen or a branched or straight-chain $C_1$- to $C_9$-alkyl radical or alkoxycarbonyl radical.

Phenol, alkylphenols, such as cresols, p-tert-butylphenol, p-cumylphenol, p-n-octylphenol, p-isooctylphenol, p-n-nonylphenol and p-isononylphenol, halophenols, such as p-chlorophenol, 2,4-dichlorophenol, p-bromophenol and 2,4,6-tribromophenol, or methyl salicylate are therefore preferred. Phenol is particularly preferred.

In the context of the invention, alkali solution is preferably to be understood as meaning sodium hydroxide solution, potassium hydroxide solution or mixtures of these, particularly preferably sodium hydroxide solution.

In the preparation of diaryl carbonates, the alkali used for the formation of the phenolate may be an alkali solution with hydroxides from the series: Na, K, Li hydroxide. Sodium hydroxide solution is preferred and is used in the novel process preferably as a 10 to 55% strength by weight solution. The alkali hydroxide or the alkali solution used may have been prepared, for example, by the amalgam process or the so-called diaphragm process in the case of sodium hydroxide or sodium hydroxide solution. Both processes have long been used and are familiar to the person skilled in the art. In the case of sodium hydroxide solution, that prepared by the diaphragm process is preferably used.

The aqueous phase in the process according to the invention for the preparation of polycarbonates contains alkali solution, one or more diphenols and water, it being possible for the concentration of this aqueous solution, based on the sum of the diphenols, calculated not as sodium salt but as free diphenol, to vary preferably between 1 and 30% by weight, particularly preferably between 3 and 25% by weight, based on the total weight of the aqueous solution. Very particularly preferably, the concentration of this aqueous solution, based on the sum of the diphenols, may vary between 3 and 8% by weight for polycarbonates having an $M_w$ of greater than 45 000 gmol$^{-1}$ and between 12 and 22% by weight for polycarbonates having an $M_w$ of 45 000 or less. In the case of higher concentrations, it may be necessary to thermostate the solutions. The alkali hydroxide used for dissolving the diphenols, e.g. sodium hydroxide or potassium hydroxide, may be used in solid form or as a corresponding aqueous alkali solution. The concentration of the alkali solution depends on the target concentration of the diphenol solution strived for but as a rule it is between 5 and 25% by weight, preferably 5 and 10% by weight, based on 100% strength alkali solution, or is chosen to be more concentrated and then diluted with water. In the process with subsequent dilution, alkali solutions having concentrations between 15 and 75% by weight, preferably 25 and 55% by weight, optionally thermostated, are used. The alkali metal content per mole of diphenol is dependent on the structure of the diphenol but as a rule is from 0.25 mol of alkali/mole of diphenol to 5.00 mol of alkali/mol of diphenol, preferably from 1.5 to 2.5 mol of alkali/mole of diphenol and, in the particularly preferred case where bisphenol A is used as the sole diphenol, from 1.85 to 2.15 mol of alkali. If more than one diphenol is used, these may be dissolved together. Since the solubility of diphenols is very greatly dependent on the amount of alkali used, it may however be advantageous to have not one solution comprising two diphenols but preferably two solutions having one diphenol each dissolved in a suitable alkali solution, which are then metered separately so that the correct mixing ratio results. Furthermore, it may be advantageous to dissolve the diphenol(s) not in alkali solution but in dilute diphenol solution provided with additional alkali. The dissolution processes may start from solid diphenol or generally in scale or prill form, or from molten diphenol. In the case of sodium hydroxide or sodium hydroxide solution, the alkali metal hydroxide used or the alkali solution, respectively, may have been prepared, for example, by the amalgam process or the so-called membrane process. Both processes have long been used and are familiar to the person skilled in the art. In the case of sodium hydroxide solution, that prepared by the membrane process is preferably used.

In such an aqueous solution and/or the aqueous phase, the diphenol(s) is or are present completely or partly in the form of the corresponding alkali metal salts or dialkali metal salts.

In the preparation of diaryl carbonates, the reaction b) can be accelerated by catalysts, such as tertiary amines, N-alkylpiperidines or onium salts. Tributylamine, triethylamine and N-ethylpiperidine are preferably used.

The amine catalyst used here may be open-chain or cyclic, triethylamine and ethylpiperidine being particularly preferred. The catalyst is used in the novel process preferably as 1 to 55% strength by weight solution.

Here, onium salts are understood as meaning compounds such as $NR_4X$, where R may be an alkyl and/or aryl radical and/or an H and X is an anion.

Phosgene can be used in process step b) in liquid or gaseous form or in solution in an inert solvent.

In step b) of the novel process, preferably used inert organic solvents are, for example, dichloromethane, toluene, the various dichloroethanes and chloropropane compounds, chlorobenzene and chlorotoluene. Dichloromethane is preferably used.

The reaction for step b) is preferably effected continuously and particularly preferably with a plug flow with little backmixing. This can therefore be effected, for example, in tubular reactors. The thorough mixing of the two phases (aqueous and organic phase) can be realised by installed orifice plates, static mixers and/or, for example, pumps.

In the preparation of diaryl carbonates, the reaction according to step b) is particularly preferably effected in two stages.

In the first stage of the preferred process, the reaction is started by combining the starting materials phosgene, the inert solvent, which preferably initially serves as a solvent for the phosgene, and the monophenol, which is preferably already dissolved beforehand in the alkali solution. In the first stage, the residence time is typically in the range of 2 seconds to 300 seconds, particularly preferably in the range of 4 seconds to 200 seconds. The pH of the first stage is preferably established by the ratio of alkali solution/monophenol/phosgene so that the pH is in the range of 11.0 to 12.0, preferably 11.2 to 11.8, particularly preferably 11.4 to 11.6. The reaction temperature of the first stage is kept preferably below 40° C., particularly preferably below 35° C., by cooling.

In the second stage of the preferred process, the reaction is completed to give the diaryl carbonate. The residence time in the preferred process is 1 minute to 2 hours, preferably 2 minutes to 1 hour, very particularly preferably 3 minutes to 30 minutes. In the second stage of the preferred process, regulation is effected by permanent monitoring of the pH (is preferably measured online by methods known in principle in the continuous process) and corresponding adjustment of the pH by addition of alkali solution. The amount of added alkali solution is in particular adjusted so that the pH of the reaction mixture in the second process stage is in the range of 7.5 to 10.5, preferably 8 to 9.5, very particularly preferably 8.2 to 9.3. The reaction temperature of the second stage is kept preferably below 50° C., particularly preferably below 40° C., very particularly preferably below 35° C., by cooling.

The parameters or explanations mentioned in general or mentioned in preferred ranges in this application can, however, also be arbitrarily combined with one another, i.e. between the respective ranges and preferred ranges.

In the preferred process for the preparation of diaryl carbonates, phosgene is used in the molar ratio 1:2 to 1:2.2 in relation to the monophenol in step b). The solvent is admixed so that the diaryl carbonate is present in a 5 to 60% strength solution, preferably 20 to 45% strength solution, after the reaction.

Suitable catalysts for the process according to the invention for the preparation of diaryl carbonates are preferably tertiary amines, such as, for example, triethylamine, tributylamine, trioctylamine, N-ethylpiperidine, N-methylpiperidine or N-isopropylpiperidine or N-n-propylpiperidine, quaternary ammonium salts, such as, for example, tetrabutylammonium, tributylbenzylammonium and tetraethylammonium hydroxide, chloride, bromide, hydrogen sulphate or tetrafluoroborate, and the phosphonium compounds corresponding to the abovementioned ammonium compounds. These compounds are described as typical phase boundary catalysts in the literature, are commercially available and are familiar to the person skilled in the art. The catalysts can be added individually, as a mixture or alongside one another and in succession to the process according to the invention, optionally also before the phosgenation, by metering after the introduction of phosgene is preferred, unless an onium compound—i.e. ammonium or phosphonium compound—or mixtures of onium compounds is or are used as catalysts. In the case of such an onium salt catalysis, addition prior to metering of the phosgene is preferred. The metering of the catalyst or of the catalysts can be effected in the absence of a solvent in an inert solvent, preferably the solvent or one of the solvents of the organic phase in the diaryl carbonate synthesis, or as an aqueous solution. In the case of the use of tertiary amines as a catalyst, for example, the metering thereof can be effected in aqueous solution as the ammonium salts thereof with acids, preferably mineral acids, in particular hydrochloric acid. With the use of a plurality of catalysts or the metering of portions of the total amount of catalyst, different metering procedures at different locations or at different times can also be carried out. The total amount of the catalysts used is between 0.0001 and 1.0 mol %, preferably between 0.001 and 0.2 mol %, based on moles of monophenols used.

For the formation of the monophenolate, preferably 1 mol of alkali/mole of monophenol to 5.00 mol of alkali/mole of monophenol, particularly preferably of 1.1 to 2.5 mol of alkali/mole of monophenol is used. The dissolution processes may start from the solid phenol or from molten phenol. The alkali hydroxide used or the alkali solution may have been prepared, for example, by the amalgam process or the so-called diaphragm process in the case of sodium hydroxide or sodium hydroxide solution. Both processes have long been used and are familiar to the person skilled in the art. In the case of sodium hydroxide solution, that prepared by the diaphragm process is preferably used.

In such an aqueous solution and/or the aqueous phase, the monophenol(s) is or are present completely or partly in the form of the corresponding alkali salts.

In the process according to the invention, one or more pump(s) are used for mixing the organic and aqueous phase and the upstream oligomerization step or aryl chloroformate preparation step. A plurality of pumps can be used in particular on the industrial scale for capacity reasons. In the case of the use of a plurality of pumps, these can be connected both in parallel and in series. Connection of a plurality of pumps in parallel would be preferred. In the process according to the invention, the pump performs the function of a mixing unit for mixing the organic and aqueous phase for the preparation of a corresponding emulsion, the function of the reaction space for the synthesis of the oligocarbonates and the function of the continuous transport of the reaction material.

The pumps used according to the invention operate according to the stator-rotor principle. As a result, in particular energy is introduced into the reaction mixture via shearing during the mixing of the two phases. The resulting emulsion has a sufficiently large phase boundary so that optimum reaction can take place at this phase boundary.

In the case of the pumps used according to the invention, the pump housing is preferably the stator and one or more rotors are present in the interior of the pump. In the case of a plurality of rotors, these are preferably mounted on the same rotor axle. The pumps used according to the invention are preferably centrifugal pumps. In preferred embodiments, these are centrifugal pumps whose rotor has a peripheral design peripheral wheel pump). In further preferred embodiments, these are centrifugal pumps whose rotor has a radial design (radial wheel pump). Pumps which operate according to the principle of the peripheral wheel pump are particularly preferred according to the invention. Such centrifugal pumps and the mode of operation thereof are known to the person skilled in the art (cf. for example DE 42 20 239 A1) and are commercially available. The principle of such a pump used according to the invention is shown by way of example and schematically in FIG. 1. Embodiments with single or multiple can enclosures, such as, for example double can enclosures, are suitable.

FIG. 1: The schematic diagram of the principal of the peripheral wheel pump having a rotating internal apparatus The abbreviations used in FIG. 1 represent 1 phosgene/solvent feed stream
2 feed stream of aqueous/alkaline sodium bisphenolate solution or sodium monophenolate solution
3 sodium hydroxide solution feed stream (NaOH feed stream)
4 reaction mixture removed
R rotating internal apparatus
S blades on the rotating internal apparatus
K circulation channel
RZ reaction inflow side (suction side)
RA reaction outflow side (pressure side)
P static housing of the peripheral wheel pump with rotating internal apparatus The peripheral wheel pump shown in FIG. 1 has a static housing P, a rotating internal apparatus R having blades S (here in the form of a paddle wheel) and a circulation channel K resulting therefrom in the housing from the suction side to the pressure side. The peripheral pump can create relatively high pressures in combination with small transported amounts and a compact design for a flow pump. During the transport, the transported reaction mixture between the blades S gives up its energy to the reaction mixture transported in the circulation channel. The pressure increase is effected by impulse exchange in that the liquid flowing at greater velocity in the blades of the rotor gives up the energy to the liquid rotating at lower velocity in the circulation channel.

The pumps used according to the invention are thermostatable, i.e. having an inlet and outlet for a thermostating liquid. The flow space for this thermostating liquid and the reaction space for the reaction material are separated from one another in such a way that no mass transfer can take place but heat exchange can.

Figure 2:
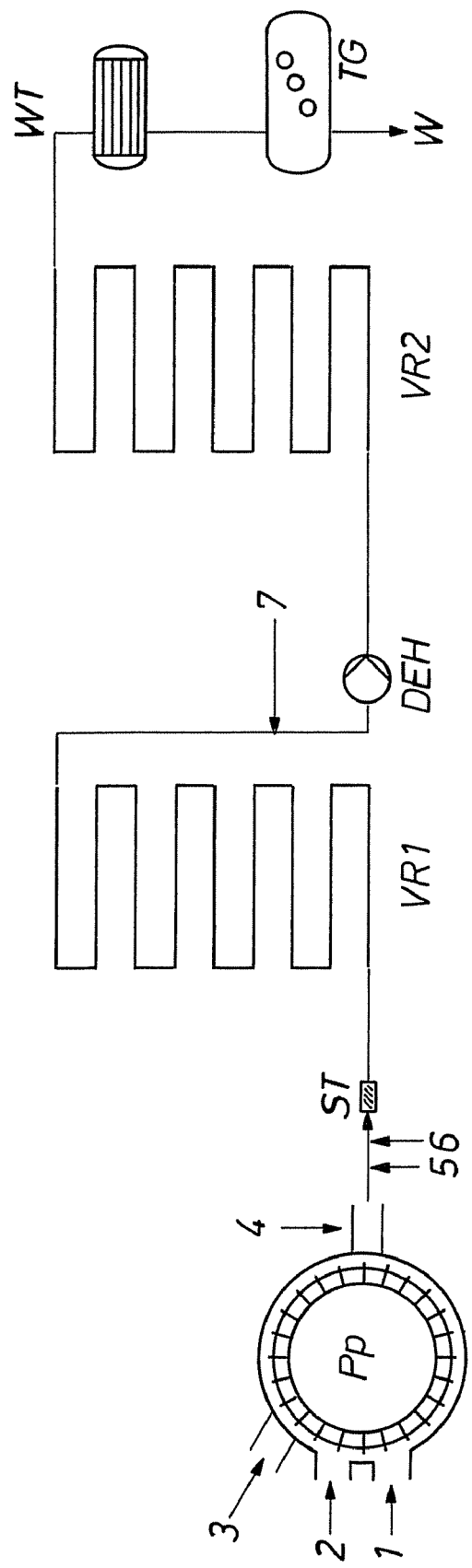
FIG. 2 is a schematic setup for the preparation of polycarbonate or diaryl carbonate by the phase boundary process using a peripheral wheel pump

The pumps used according to the invention have, as a feed to the reaction space, at least one entrance in each case for the organic and the liquid phase and at least one exit for the oligocarbonate-containing reaction mixture (in the polycarbonate preparation), or for the reaction mixture formed in the 1$^{st}$ step in the diaryl carbonate preparation (cf. FIG. 1). In preferred embodiments, further entrances for additional alkali solution and/or diphenol(ate) solution or monophenol(ate) solution and optionally for chain terminators and branching agents are preferred. The catalyst is preferably added to a downstream dwell reactor at a later time. A schematic exemplary setup for such a reaction procedure according to the invention is shown in FIG. 2. The diagram in FIG. 2 is to be considered merely by way of example with regard to the number of downstream dwell reactors. More or less than two dwell reactors can also be connected downstream.

FIG. 2: Schematic setup for the preparation of polycarbonate or diaryl carbonate by the phase boundary process using a peripheral wheel pump The abbreviations used in FIG. 2 represent 1 phosgene/solvent feed stream
2 feed stream of aqueous/alkaline sodium bisphenolate solution or sodium monophenolate solution
3 first sodium hydroxide solution feed stream (NaOH feed stream 1)
4 reaction mixture removed
5 second sodium hydroxide solution feed stream (NaOH feed stream 2)
6 chain terminator in the preparation of polycarbonate or catalyst in the preparation of diaryl carbonate (optionally)
7 catalyst
Pp peripheral wheel pump
ST static mixer
VR1 dwell reactor 1
VR2 dwell reactor 2 (optional)
WT heat exchanger
DEN pressure boost pump
TG separation vessel
w subsequent wash In a further embodiment of the process according to the invention, a pump circulation reactor, instead of a dwell reactor, can also be connected downstream of the pump used according to the invention. This embodiment of the process according to the invention would have the advantage that existing plants could be used by connecting a pump used according to the invention upstream without far-reaching conversions of the plants being required. A schematic exemplary setup for such a reaction procedure according to the invention is shown in FIG. 2a. The diagram in FIG. 2a is to be regarded merely by way of example with regard to the number of downstream dwell reactors. More or less than two dwell reactors can also be connected downstream.

In a process variant with the pump circulation reactor connected downstream of the pump used according to the invention, the starting materials, such as, for example, the diphenolate solution or monophenolate solution or the first sodium hydroxide feed stream, either be added completely to the pump or optionally fed proportionately firstly to the downstream pump circulation reactor.

FIG. 2a: Schematic setup for the preparation of polycarbonate or diaryl carbonate by the phase boundary process using a peripheral wheel pump with downstream pump circulation reactor The abbreviations used in FIG. 2a in addition to those used in FIG. 2 represent 2' optional feed stream of a proportion of aqueous/alkaline sodium bisphenolate solution or sodium monophenolate solution
3' optional feed stream of a proportion of the first sodium hydroxide solution feed stream NaOH feed stream 1')
EG devolatilization vessel
UR pump circulation reactor
AT discharge pump
P pump for maintaining the circulation The residence time of the reaction mixture in the pump used according to the invention is preferably 20 seconds to 10 minutes, particularly preferably 30 seconds to 5 minutes and very particularly preferably 30 seconds to 3 minutes.

For regulating the molecular weight of the polycarbonate, the addition of one or more monofunctional chain terminator(s), such as phenol or alkylphenols, in particular phenol, p-tert-butylphenol, isooctylphenol, cumylphenol, the chlorocarbonic acid esters thereof or acid chlorides of monocarboxylic acids or mixtures of these chain terminators may optionally be required. Such chain terminators are optionally either fed to the reaction with dihydroxydiarylalkane(s) or added to the synthesis at any desired time during the synthesis as long as phosgene or chlorocarbonic acid terminal groups are still present in the reaction mixture, in the case of the acid chlorides and chlorocarbonic acid esters as chain terminators, as long as sufficient phenolic terminal groups of the resulting polymer are available. Preferably, however, the chain terminator or terminators are added after the phosgenation at a place or at a time where or when phosgene is no longer present but the catalyst has not yet been metered in, i.e. they can be metered in before the catalyst, together with the catalyst or parallel thereto.

In the same way, in the preparation of polycarbonates, one or more branching agents or mixtures of branching agents can optionally be added to the synthesis. Usually, however, such branching agents are added before the chain terminator(s). For example, trisphenols, quarterphenols, acid chlorides of tri- or tetracarboxylic acids or mixtures of the polyphenols or of the acid chlorides are used as branching agents.

Examples of compounds suitable as branching agents and having three or more than three phenolic hydroxyl groups are phloroglucinol, 4,6-dimethyl-2,4,6-tri(4-hydroxyphenyl)-hept-2-ene, 4,6-dimethyl-2,4,6-tri(4-hydroxyphenyl)heptane, 1,3,5-tri(4-hydroxyphenyl)benzene, 1,1,1-tri(4-hydroxyphenyl)ethane, tri(4-hydroxyphenyl)phenylmethane, 2,2-bis(4,4-bis(4-hydroxyphenyl)cyclohexyl]propane, 2,4-bis(4-hydroxyphenylisopropyl)phenol, tetra(4-hydroxyphenyl)methane.

Examples of other trifunctional compounds suitable as branching agents are 2,4-dihydroxybenzoic acid, trimesic acid, cyanuric chloride and 3,3-bis(3-methyl-4-hydroxyphenyl)-2-oxo-2,3-dihydroindole.

Particularly preferred branching agents are 3,3-bis(3-methyl-4-hydroxyphenyl)-2-oxo-2,3-dihydroindole and 1,1,1-tri(4-hydroxyphenyl)ethane.

Suitable catalysts for the process according to the invention for the preparation of polycarbonates are preferably tertiary amines, such as, for example, triethylamine, tributylamine, trioctylamine, N-ethylpiperidine, N-methylpiperidine or N-iso/n-propylpiperidine, quaternary ammonium salts, such as, for example, tetrabutylammonium, tributylbenzylammonium, or tetraethylammonium hydroxide, chloride, bromide, hydrogen sulphate or tetrafluoroborate, and the phosphonium compounds corresponding to the abovementioned ammonium compounds. These compounds are described in the literature as typical phase boundary catalysts, are commercially available and are familiar to the person skilled in the art. The catalysts can be added to the process according to the invention individually, as a mixture or side by side and in succession, optionally also before the phosgenation, but meterings after the phosgene introduction are preferred, unless an onium compound—i.e. ammonium or phosphonium compound—or mixtures of onium compounds are used as catalysts. In the case of such an onium salt catalysis, an addition before the phosgene metering is preferred. The metering of the catalyst or of the catalysts can be effected as such, in an inert solvent, preferably a solvent or one of the solvents of the organic phase in the polycarbonate synthesis, or as aqueous solution. In the case of the use of tertiary amines as a catalyst, for example, the metering thereof can be effected in aqueous solution as the ammonium salts thereof with acids, preferably mineral acids, in particular hydrochloric acids. With the use of a plurality of catalysts or the metering of portions of the total amount of catalyst, it is of course also possible to carry out different metering procedures at different places and at different times. The total amount of the catalyst used is between 0.001 and 10 mol %, preferably 0.01 to 8 mol %, particularly preferably 0.05 to 5 mol %, based on moles of diphenols used.

In the context of the invention, oligocarbonates are preferably those of the general formulae (I), (II) and/or (III),

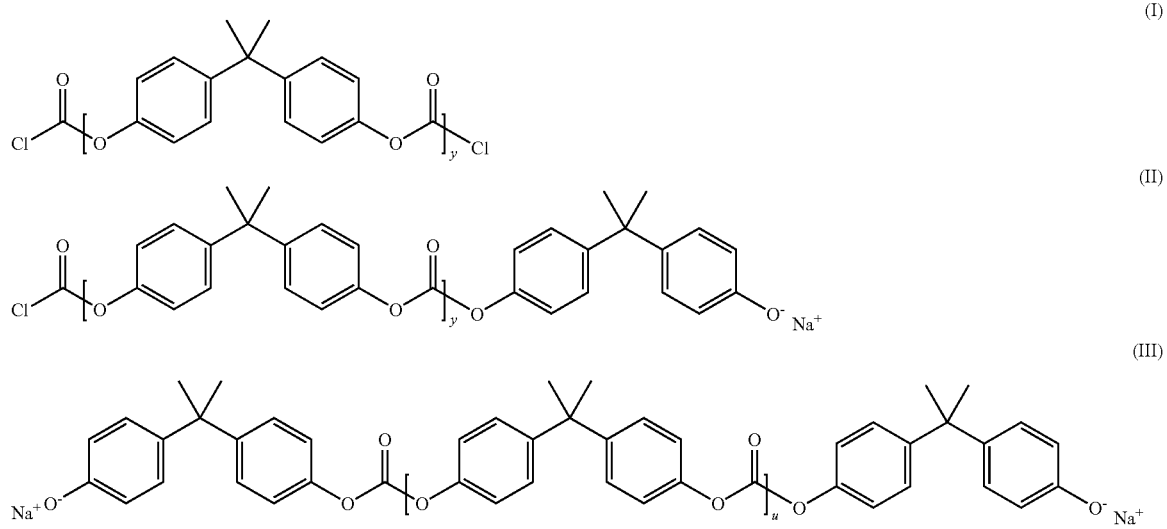

in which u represents 0 or an integer from 1 to 20, preferably represents 0 or an integer from 1 to 12, particularly preferably represents 0 or an integer from 1 to 8, y represents an integer from 1 to 20, preferably from 1 to 12, particularly preferably from 1 to 8, and z represents 0 or an integer from 1 to 20, preferably represents 0 or an integer from 1 to 12, particularly preferably represents 0 or an integer from 1 to 8.

Such oligomers preferably have an average molecular weight $M_w$ of up to 5000 g/mol, preferably up to 3500 g/mol, very particularly preferably up to 2000 g/mol.

The average molecular weight averages stated in the context of this application are weight averages ($M_w$) which were determined by gel permeation chromatography (GPC) using polycarbonate as a standard. The detection of the eluate signal can be effected, for example, by using the refractive index or by UV absorption in the region of for example 254 nm.

From the pump or pumps, the oligocarbonate-containing reaction mixture or aryl chloroformate- and/or diaryl carbonate-containing reaction mixture is condensed in at least one reactor with addition of further alkali solution, optionally chain terminator(s) and optionally at least one further catalyst to give polycarbonates or reacted to give diaryl carbonates. In preferred embodiments, this reaction is effected in a cascade of a plurality of reactors connected in series. Suitable reactors for the reaction are any desired reactor designs, such as, for example, stirred tanks, tubular reactors, pump circulation reactors, cascades thereof and combinations thereof (cf. for example FIG. 2 or FIG. 5).

For working up the at least two-phase reaction mixture still containing traces, preferably less than 2 ppm, of chlorocarbonic acid esters which is reacted in the polycarbonate preparation, settling is allowed for phase separation. The aqueous alkaline phase is optionally recycled wholly or partly to the polycarbonate synthesis as an aqueous phase or fed to the wastewater working up where solvent and catalyst fractions are separated off and optionally recycled to the polycarbonate synthesis. In another variant of the working up, after the organic impurities have been separated off, in particular from solvents and polymer residues, and optionally after a certain pH has been established, for example by addition of sodium hydroxide solution, the salt is separated off and can be fed, for example, to the chloralkali electrolysis, while the aqueous phase is optionally fed back to the polycarbonate synthesis.

For working up the at least two-phase reaction mixture completely reacted in the diaryl carbonate preparation and still containing at most traces, preferably less than 2 ppm, of aryl chloroformates, settling is allowed for phase separation. Aqueous alkaline phase is fed, optionally completely or partly in combination with wash phases, to the wastewater working-up, where solvent and catalyst fractions are separated off by stripping and optionally recycled into the diaryl carbonate synthesis. In another variant of the working-up, after the organic impurities, in particular solvents and catalyst residues, have been separated off and optionally after a certain pH has been established, for example by addition of hydrochloric acid, the salt solution is separated off and can be fed, for example, to the chlor-alkali electrolysis, while the aqueous phase is optionally recycled to the diaryl carbonate synthesis.

The organic phase containing the polycarbonate or diaryl carbonate can then be purified in various ways known to the person skilled in the art for removing the alkaline, ionic or catalytic contaminations.

Even after one or more settling processes, optionally supported by passages through settling tanks, stirred tanks, coalescers or separators and combinations of these measures—it optionally being possible to meter in water in each separation step or some separation steps, in certain circumstances with the use of active or passive mixing members—the organic phase still contains proportions of the aqueous alkaline phase in fine droplets and of the catalyst(s). After this coarse separation of the alkaline, aqueous phase, the organic phase can be washed once or several times with dilute acids, mineral acids, carboxylic acids, hydroxycarboxylic acids and/or sulphonic acids. Aqueous mineral acids, in particular hydrochloric acid, phosphorus acid, phosphoric acid or mixtures of these acids are preferred. The concentration of these acids should preferably be in the range of 0.001 to 50% by weight, preferably 0.01 to 5% by weight. Furthermore the organic phase can be repeatedly washed with desalinated or distilled water. The separation of the organic phase, optionally dispersed with parts of the organic phase, after the individual wash steps is effected by means of settling tanks, stirred tanks, coalescers or separators or combinations of these measures, it being possible to meter in the wash water between the wash steps, optionally with the use of active or passive mixing members. In the polycarbonate preparation, between these wash steps or after the washing, acids, preferably dissolved in the solvent on which the polymer solution is based, can optionally be added. Hydrogen chloride gas, phosphoric acid or phosphorus acid, which can optionally also be used as mixtures, are preferably used here. The purified polycarbonate solution thus obtained should preferably contain not more than 5% by weight, preferably less than 1% by weight, very particularly preferably less than 0.5% by weight, of water after the last separation process.

The isolation of the diaryl carbonate from the solution can be effected by evaporation of the solvent by means of temperature, vacuum or a heated entraining gas or preferably distillation.

The diaryl carbonates prepared by the process according to the invention are distinguished by particularly high purity (GC>99.95%) and very good transesterification behaviour, so that a polycarbonate can be subsequently prepared therefrom in excellent quality.

The use of the diaryl carbonates for the preparation of aromatic oligocarbonates/polycarbonates by the melt transesterification process is known from the literature and is described, for example, in Encyclopedia of Polymer Science, Vol. 10 (1969), Chemistry and Physics of Polycarbonates, Polymer Reviews, H. Schnell, Vol. 9, John Wiley and Sons, Inc. (1964) or U.S. Pat. No. 5,340,905.

The isolation of the polycarbonate from the solution can be effected by evaporation of the solvent by means of temperature, vacuum or a heated entraining gas. Other isolation methods are, for example, crystallization and precipitation.

If the concentration of the polycarbonate solution and possibly also the isolation of the polycarbonate are effected by distilling off the solvent, optionally by superheating and expansion, the term "flash process" is used. Such a process is known to the person skilled in the art and is described, for example, in "Thermische Trennverfahren [Thermal separation processes]", VCH Verlagsanstalt 1988, page 114. If instead a heated carrier gas is sprayed together with the solution to be evaporated down, the term "spray evaporation/spray drying" is used, which is described by way of example in Vauck, "Grundoperationen chemischer Verfahrenstechnik [Basic operations of chemical process engineering]", Deutscher Verlag für Grundstoffundustrie 2000, 11th edition, page 690. All these processes are described in the patent literature and in textbooks and are familiar to the person skilled in the art.

On removal of the solvent by temperature (distilling of) or the technically more effective flash process, highly concentrated polycarbonate melts are obtained. In the flash process, polymer solutions are repeatedly heated under slightly superatmospheric pressure to temperatures above the boiling point under atmospheric pressure and these solutions superheated relative to atmospheric pressure are then let down into a vessel at low pressure, e.g. atmospheric pressure. It may be advantageous to ensure that the concentration stages, or in other words the temperature stages of the superheating, are not chosen to be too large but preferably to choose a two- to four-stage process.

The residues of the solvent can be removed from the highly concentrated polycarbonate melts thus obtained either directly from the melt by means of vented extruders (cf. for example BE-A 866 991, EP-A 0 411 510, U.S. Pat. No.

4,980,105, DE-A 33 32 065), thin-film evaporators (cf. for example EP-A 0 267 025), falling-film evaporators, strand evaporators or friction compacting (cf. for example EP-A 0 460 450), optionally also with addition of an entraining agent, such as nitrogen or carbon dioxide, or with the use of a vacuum (cf. for example EP-A 0 039 96, EP-A 0 256 003, U.S. Pat. No. 4,423,207), alternatively also by subsequent crystallization (cf. for example DE-A 34 29 960) and/or expulsion of the residues of the solvent by heating in the solid phase (cf. for example U.S. Pat. No. 3,986,269, DE-A 20 53 876). These processes too and the apparatuses required for this purpose are described in the literature and are familiar to the person skilled in the art.

Polycarbonate granules can—if possible—be obtained by direct spinning of the melt and subsequent granulation or by use of discharge extruders from which spinning is effected in air or under liquid, generally water. If extruders are used, additives can be added to the polycarbonate melt before the extruder, optionally with use of static mixers or by side extruders in this extruder.

Alternatively, the polycarbonate solution can be subjected to a spray evaporation. During spraying, the polycarbonate solution, optionally after heating, is either sprayed into a vessel at reduced pressure or sprayed by means of a nozzle with a heated carrier gas, e.g. nitrogen, argon or steam, into a vessel at atmospheric pressure. In both cases, powders (dilute) or flakes (concentrated) of the polymer are obtained, depending on the concentration of the polymer solution, from which the last residues of the solvent optionally also have to be removed as above. Thereafter, granules can be obtained by means of a compounding extruder and subsequent spinning. Here too, additives as described above can be added in the periphery or to the extruder itself. Often, it may be necessary to pass through a compacting step for the polymer powder before the extrusion owing to the low bulk density of the powders and flakes.

Alternatively, the polymer can be substantially precipitated from the washed and optionally still concentrated polycarbonate solution by addition of a nonsolvent for polycarbonate. The nonsolvents act as precipitating agents. Here, it is advantageous first to add a small amount of the nonsolvent and optionally also to allow waiting times between the additions of the batches of nonsolvent. It may also be advantageous to use different nonsolvents. For example aliphatic or cycloaliphatic hydrocarbons, in particular heptane, isooctane or cyclohexane, alcohols, such as, for example, methanol, ethanol or isopropanol, ketones, such as, for example, acetone, or mixtures of these are used as precipitating agents here. During the precipitation, as a rule the polymer solution is slowly added to the precipitating agent. The polycarbonates thus obtained are processed to granules as described in the case of the spray evaporation and additives are optionally introduced.

According to other processes, precipitation and crystallization products or amorphously solidified products are crystallized in fine-particle form by passing over vapours of one or more nonsolvents for polycarbonate, with simultaneous heating below the glass transition temperature, and are further condensed to give higher molecular weights. If the oligomers optionally have different terminal groups (phenolic and chain terminator ends), the term solid-phase condensation is used.

The addition of additives serves for increasing the duration of use or improving the colour stability (stabilizers), simplifying the processing (e.g. demoulding agents, flow improvers, antistatic agents) or adapting the polymer properties to certain loads (impact modifiers, such as rubbers; flameproofing agents, colorants, glass fibres).

These additives can be added to the polymer melt individually or together in any desired mixtures or in a plurality of different mixtures. This can be effected directly during the isolation of the polymer or after melting of granules in a so-called compounding step. The additives or the mixtures thereof can be added as a solid, preferably as powder, or as melt to the polymer melt. Another method of metering is the use of masterbatches or mixtures of masterbatches of the additives or additive mixtures.

Suitable additives are described, for example, in "Additives for Plastics Handbook, John Murphy, Elsevier, Oxford 1999", and in "Plastics Additives Handbook, Hans Zweifel, Hanser, Munich 2001".

Examples of suitable antioxidants or heat stabilizers are:

alkylated monophenols, alkylthiomethylphenols, hydroquinones and alkylated hydroquinones, tocopherols, hydroxylated thiodiphenyl ethers, alkylidenebisphenols, O-, N- and S-benzyl compounds, hydroxybenzylated malonates, aromatic hydroxybenzyl compounds, triazine compounds, acylaminophenols, esters of β-(3,5-di-tert-butyl-4-hydroxyphenyl)propionic acid, esters of β-(5-tert-butyl-4-hydroxy-3-methylphenyl)propionic acid, esters of β-(3,5-dicyclohexyl-4-hydroxyphenyl)propionic acid, esters of 3,5-di-tert-butyl-4-hydroxyphenylacetic acid, amides of β-(3,5-di-tert-butyl-4-hydroxyphenyl)propionic acid, suitable thiosynergistic agents, secondary antioxidants, phosphites, phosphonites, phosphonates and phosphanes, benzofuranones and indolinones.

Preferred antioxidants or heat stabilizers are organic phosphites, phosphonates and phosphanes, generally those in which the organic radicals completely or partially comprise optionally substituted aromatic radicals.

Suitable complexing agents for heavy metals and for neutralization of traces of alkali are, for example, o- or m-phosphoric acids, completely or partly esterified phosphates or phosphites.

Suitable light stabilizers (UV absorbers) are, for example, 2-(2'-hydroxyphenyl)benzotriazoles, 2-hydroxybenzophenones, esters of substituted and unsubstituted benzoic acids, acrylates, sterically hindered amines, oxamides, 2-(2-hydroxyphenyl)-1,3,5-triazines or substituted benzotriazoles; substituted benzotriazoles are particularly preferred.

Polypropylene glycols alone or in combination with, for example, sulphones or sulphonamides as stabilizers can be used to prevent damage by gamma-rays.

These and other stabilizers can be used individually or in combinations and are added in said forms to the polymer.

In addition, processing auxiliaries, such as demoulding agents, such as, for example, derivatives of long-chain fatty acids, may be added. For example, pentaerythrityl tetrastearate and glyceryl monostearate are preferred. They are used alone or as a mixture, preferably in an amount of 0.02 to 1% by weight, based on the mass of the composition. Suitable flame-retardant additives are phosphate esters, i.e. triphenyl phosphate, resorcinol diphosphoric acid esters, bromine-containing compounds, such as brominated phosphoric acid esters, brominated oligocarbonates and polycarbonates, and preferably salts of fluorinated organic sulphonic acids. Suitable impact modifiers are butadiene rubber with grafted-on styrene-acrylonitrile or methyl methacrylate, ethylene-propylene rubbers with grafted-on maleic anhydride, ethyl acrylate and butyl acrylate rubbers with grafted-on methyl methacrylate or styrene-acrylonitrile, interpenetrating siloxane and acrylate networks with grafted-on methyl methacrylate or styrene-acrylonitrile.

Furthermore, colorants, such as organic dyes or pigments and inorganic pigments, IR absorbers, may be added, individually, as a mixture or in combination with stabilizers, glass fibres, (hollow) glass spheres or inorganic fillers.

Polycarbonate melts which were produced by isolation of the polymer or by compounding can be spun in strand form through a die head and cooled with gas, e.g. air or nitrogen, or a cooling liquid, generally water, and the solidified strands can be granulated in commercially available granulators with cutters which are present, for example, on a rotating roll, in air, under inert gas, such as nitrogen or argon, or under water. Depending on the design of the apparatus column-like granules having a round or elliptical cross section and rough or smooth surface form are formed. The cut edges may be smooth or have a glass-like fracture with broken cut edges or remaining residues on the cut edges. Granules which are formed as uniformly as possible and have as few remaining projections as possible on the cut edges are desirable. Furthermore, the dust fraction in the granules should be kept as low as possible, preferably below 100 mg/kg of granules. The diameter of the granule particles should be between 0.5 mm and 10 mm, preferably 1 to 8 mm, particularly preferably 3 to 6 mm. While the length of the granule particles should be between 1 and 10 mm, preferably between 2 and 8 mm, and the weight between 10 and 50 mg, preferably between 15 and 30 mg. Granules whose ratio of diameter, of the average diameter in the case of an elliptical cross section, to length is 0.8 to 1.2 are preferred, and granules having a ratio of about 1 are particularly preferred. These parameters are subject to size distributions, distributions as narrow as possible are preferred, i.e. granules having dimensions as uniform as possible.

Cooling, spinning, granulation and the subsequent transport or the conveying of the granules with gas or liquid and the subsequent storage, optionally after a mixing or homogenization process, should be designed so that, in spite of any static charge build-up present, as far as possible no impurities are applied to the polymer surface, strand surface or granule surface, such as, for example, dust, abrasion material from the machines, aerosol-like lubricants and other liquids and salts from water baths or cooling systems possibly used.

The present application likewise relates to the polymers prepared by the process according to the invention.

The polymers prepared by the process according to the invention have a narrow molecular weight distribution, preferably even one narrower than those prepared according to the prior art by the phase boundary process. Preferably, the polymers prepared by the process according to the invention have a nonuniformity N of 1.1 to 1.6 (depending on the viscosity of the polycarbonates prepared).

The polycarbonates prepared according to the invention are suitable, for example, for the production of extrudates and mouldings, in particular those for use in the transparent area, very particularly in the area of optical applications, such as, for example, sheets, multi-wall sheets, glazings, diffuser screens, lamp coverings or optical data stores, such as audio CD, CD-R(W), DVD, DVD-R(W), minidiscs in their various read-only or recordable and optionally also rewritable embodiments.

Examples of further applications, but without limiting the subject of the present invention, are:
1. Safety screens, which are known to be required in many areas of buildings, vehicles and aircraft, and as visors of helmets.
2. Sheets.
3. Blow-moulded bodies (also see U.S. Pat. No. 2,964, 794), for example 1 to 5 gallon water bottles.
4. Transparent sheets, such as solid sheets, in particular hollow-chamber sheets, for example for covering buildings, such as railway stations, greenhouses and lighting systems.
5. Optical data stores, such as audio CDs, CD-R(W)s, DCDs, DVD-R(W)s, minidiscs and the subsequent developments.
6. Traffic light housings or traffic signs.
7. Foams having an open or closed optionally printable surface.
8. Filaments and wires (see also DE-A 11 37 167).
9. Lighting applications, optionally with the use of glass fibres for applications in the translucent area.
10. Translucent formulations containing barium sulphate and/or titanium dioxide and/or zirconium oxide or organic polymeric acrylate rubbers (EP-A 0 634 445, EP-A 0 269 324) for the production of transparent and light-scattering shaped articles.
11. Precision injection-moulded parts, such as holders, e.g. lens holders; polycarbonates comprising glass fibres and an optionally additional content of 1-10% by weight of molybdenum disulphide (based on the total moulding area) are optionally used here.
12. Optical instrument parts, in particular lenses for photographic cameras and cine cameras (DE-A 27 01 173).
13. Light transmission media, in particular optical fibres (EP-A 0 089 801) and lighting strips.
14. Electrical insulation materials for electrical conductors and for plug housings and connectors and capacitors.
15. Mobile telephone housings.
16. Network interface devices.
17. Carrier materials for organic photoconductors.
18. Lights, headlight lamps, light diffuser screens or inner lenses.
19. Medical applications, such as oxygenators or dialysers.
20. Food applications, such as bottles, crockery and chocolate moulds.
21. Applications in the automotive sector, such as glazings or in the form of blends with ABS as bumpers.
22. Sports articles, such as slalom poles or ski boot fasteners.
23. Household articles, such as kitchen sinks, wash basins, letterboxes.
24. Housings, such as electrical distributor boxes.
25. Housings for electrical devices, such as toothbrushes, hair-dryers, coffee machines, machine tools, such as drills, cutters, planes and saws.
26. Washing machine port holes.
27. Safety goggles, sunglasses, corrective glasses or lenses thereof.
28. Lamp coverings.
29. Packaging films.
30. Chip boxes, chip supports, boxes for Si wafers.
31. Other applications, such as animal shed doors or animal cages.

Surprisingly, the diphenol pollution or monophenol pollution of the wastewater could also be reduced by the process according to the invention.

The use of pumps having a triple function as mixing unit, reaction space for the oligomerization step or aryl chloroformate and/or diaryl carbonate preparation step and conveying unit has not been described in the literature for the phase boundary process for the preparation of polycarbonates or diaryl carbonates. The present invention therefore furthermore relates to the use of one or more pump(s) for the continuous preparation of polycarbonate or diaryl carbonate by the phase boundary process, the pump(s)

operating according to the stator-rotor principle,
being thermostatable and
having at least in each case one entrance for an organic and an aqueous phase and optionally further entrances for chain terminators, branching agents and/or additionally alkali solution, catalyst and at least one exit for the oligocarbonate-containing mixture or aryl chloroformate- and/or diaryl carbonate-containing mixture, characterized in that, in this pump or these pumps, both the continuous mixing of the organic and aqueous phase, the organic phase containing at least one solvent suitable for the polycarbonate or diaryl carbonate and some or all of the phosgene and the aqueous phase containing the diphenol(s) or monophenol(s), water and alkali solution, and the reaction of the diphenol(s) or monophenol(s) and phosgene to give oligocarbonates or aryl chloroformates and/or diaryl carbonates are effected.

The pumps already described above for the process according to the invention are suitable for this use. Centrifugal pumps, particularly preferably peripheral wheel pumps, are particularly suitable for this purpose.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

In a continuous phase boundary process, polycarbonates were prepared by means of different reactor concepts in each case. In the experiments, the influence of the use according to the invention of the special pump prepared with known reactors, such as pump circulation reactors or nozzles, was investigated with otherwise identical reaction settings.

In all examples, the reaction was carried out continuously in an emulsion comprising water and a solvent mixture of 50% by weight of methylene chloride and 50% by weight of chlorobenzene. The chain terminator used was p-tert-butylphenol (BUP). The catalyst used was n-ethylpiperidine (FPP). The polycarbonate solution obtained after the aqueous phase had been separated off after passing through the dwell cascade comprising the four reactors NR1 to NR4 in FIGS. 3 and 5 was washed acidic with hydrochloric acid and then washed neutral by means of disc separators with demineralized water. The polycarbonate solutions washed in this manner were dried and were then concentrated by evaporation of the solvent. Complete removal of the residual solvent in a vacuum drying oven at 100° C. led to the polycarbonate.

In all examples, the procedure was effected with the following reaction settings:
Na bisphenolate solution: throughput 910.3 g/h (0.598 mol of bisphenol A/h), Na bisphenolate content: 15.0% by weight of Na bisphenolate, based on the total weight of the solution
Phosgene: 72.18 g/h (0.73 mol/h)
Solvent: 737.7 g/h (solvent mixture of 50% by weight of methylene chloride and 50% by weight of chlorobenzene)
Sodium hydroxide solution: 113.9 g/h; NaOH content: 44% by weight of NaOH, based on the total weight of the sodium hydroxide solution, for dissolving 136.5 g of bisphenol A
Sodium hydroxide solution after first reactor: 49.5 g/h; NaOH content: 44% by weight of NaOH, based on the total weight of the sodium hydroxide solution
Chain terminator BUP: 3.594 g/h (in 140.2 g/h of solvent mixture 50:50)
Catalyst EPP: 0.677 g/h; (in 6.2 g/h of solvent 50:50)
Phosgene/bisphenol A: 122 mol % of phosgene, based on the amount of bisphenol A
EPP/bisphenol A: 1.0 mol % of EPP, based on the amount of bisphenol A
BUP/bisphenol A: 4.0 mol % of BUP, based on the amount of bisphenol A
Reaction temperature: 34° C.
Polycarbonate content: 15.0% by weight of polycarbonate, based on the total weight of the solution, dissolved in abovementioned solvent
Addition of the chain terminator after the first reactor The addition of the chain terminator was effected in all examples in such a way that a comparable relative viscosity ($\eta_{rel}$) was achieved for the end products.

Example 1

Comparative Example

Figure 3:
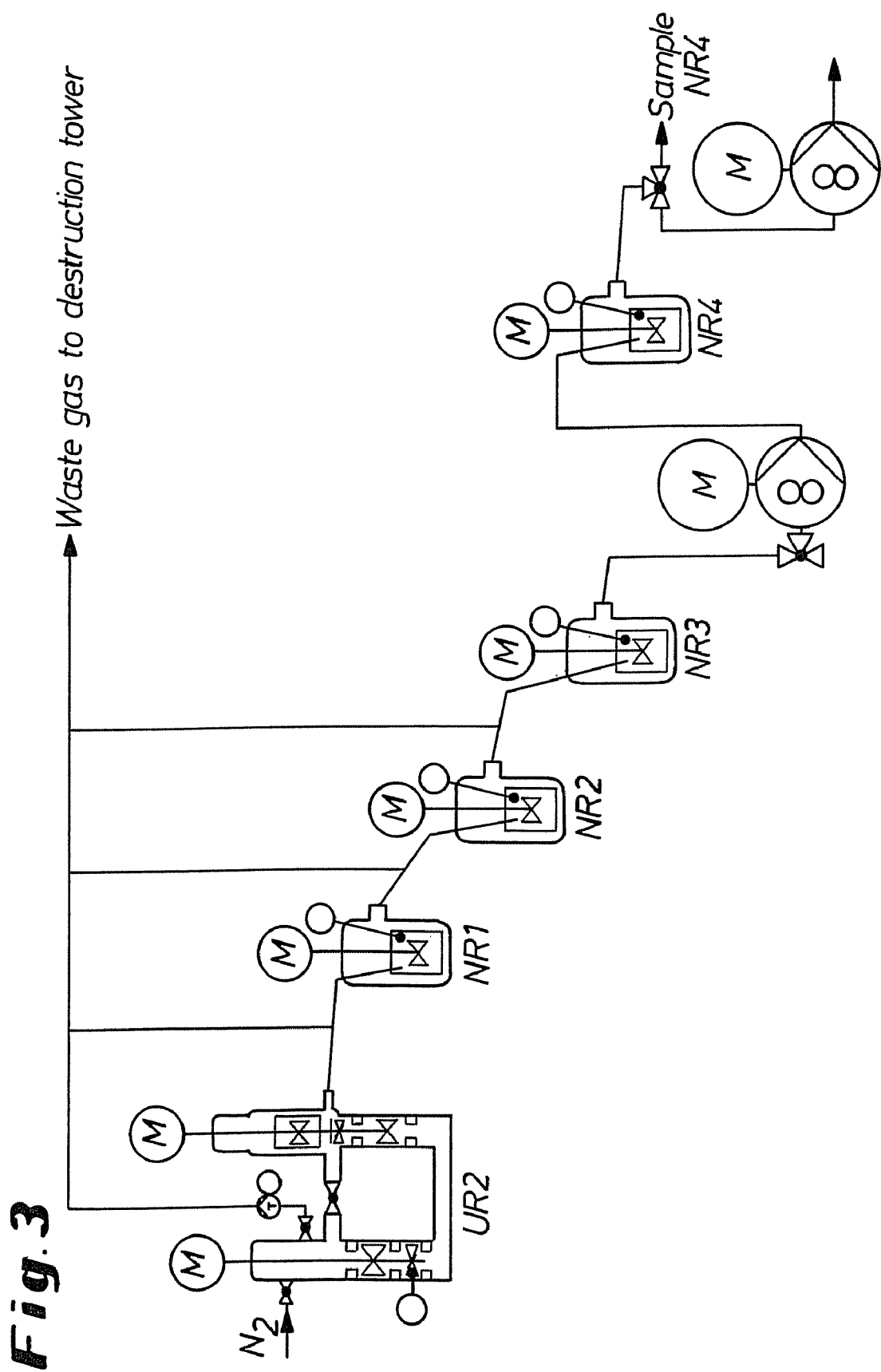
FIG. 3 is an experimental setup used for the preparation of polycarbonate using a state of the art glass pump circulation reactor UR 2 (comparative example)
Figure 4:
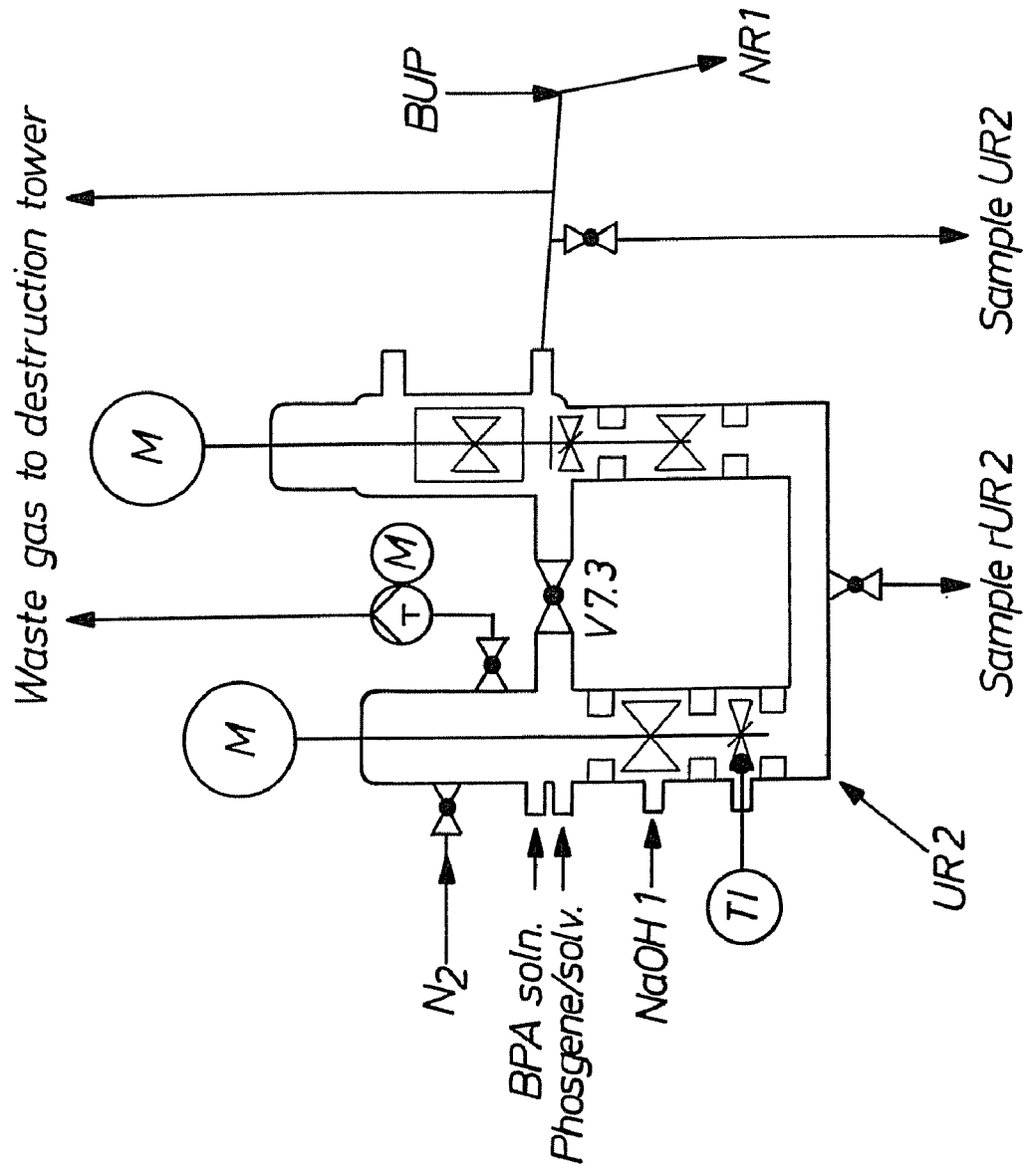
FIG. 4 is a schematic setup of the glass pump circulation reactor UR 2 used in the comparative example.

Polycarbonate was prepared according to the experimental setup in FIG. 3. A glass pump circulation reactor UR 2 according to FIG. 4 to which a dwell cascade of four stirred tanks (postreactors NR1 to NR4) for the postreaction are connected was used. In the individual reactors, the stirring elements were driven by motors M. In addition, two gear pumps with motor M were present before and after the last postreactor NR4. Na bisphenolate solution, phosgene in the abovementioned solvents and sodium hydroxide solution were fed continuously to the pump circulation reactor in the above-mentioned amount and back-mixed by circulating with valve V7.3 open. The stirrer used in the pump circulation reactor was operated at 1000 revolutions/min. At the outlet of the pump circulation reactor, the reaction mixture was discharged continuously from the pump circulation reactor, mixed with a chain terminator and passed into the dwell cascade of four stirred tanks, shown in FIG. 3, for the postreaction. The catalyst was fed to the third postreactor NR3.

Example 2

Comparative Example

The same experimental setup as in Example 1 was used, but the valve V7.3 was closed in the pump circulation reactor UR 2 so that back-mixing was ruled out. As a result, the pump circulation reactor UR 2 functioned as a normal nozzle.

Example 3

According to the Invention

Instead of the pump circulation reactor UR 2 in Example 1, a peripheral wheel pump RM according to FIG. 1 was used. Otherwise, the same experimental setup was used as in Example 1 (cf. FIG. 5). Na bisphenolate solution, phosgene in the above-mentioned solvents and sodium hydroxide solution were fed continuously to the pump RM in the abovementioned amount and mixed by the rotating peripheral wheel provided with blades. At the outlet of the pump RM, the reaction mixture was discharged continuously from the interior of the pump, mixed with a chain terminator and passed into the dwell cascade of four stirred tanks, shown in FIG. 5, for the postreaction. The catalyst was fed to the third postreactor NR3.

Tab. 1 shows the results with regard to the polycarbonate obtained and the pollution of the resulting wastewater with bisphenol A (BPA).

TABLE 1

| Example | BPA content in the wastewater [ppm by weight] | $M_w$ [g/mol] | U | $\eta_{rel}$ |
|---|---|---|---|---|
| 1 | 238 | 19 182 | 1.54 | 1.215 |
| 2 | 675 | 19 111 | 1.69 | 1.214 |
| 3 | 48 | 19 353 | 1.51 | 1.218 |

The relative solution viscosity $\eta_{rel}$ was determined in dichloromethane as solvent at a concentration of 5 g/l and at a temperature of 25° C. using an Ubbelohde viscometer.

The BPA content in the wastewater was determined by means of HPLC and UV detection (245 nm) after calibration with the BPA.

The results show a substantial reduction of the wastewater pollution with BPA with the use according to the invention of the special pump compared with the conventional preparation by means of the pump circulation reactor or simple nozzle. When the phase boundary process is carried out according to the invention an increase in the phosgene and sodium hydroxide solution addition for completing the conversion of the diphenol is therefore not necessary. The process carried out according to the invention is therefore also more economical than according to the known processes. The nonuniformity N, which is a measure of the broadness of the molecular weight distribution of the resulting polycarbonate, could also be slightly reduced compared with the products obtainable by known processes.

The invention claimed is:

1. A process for continuously preparing a polycarbonate or a copolycarbonate or a diaryl carbonate by the phase boundary process from a diphenol or a monophenol, phosgene and a catalyst, optionally in the presence of at least one chain terminator and/or branching agent, comprising
   (a) continuously mixing an organic phase and an aqueous phase, said organic phase comprising a solvent suitable for said polycarbonate or copolycarbonate or diaryl carbonate and phosgene and said aqueous phase comprising said a diphenol or a monophenol, water, and alkali solution;
   (b) reacting said diphenol or monophenol and said phosgene in the presence of a catalyst to give a polycarbonate or a copolycarbonate or an aryl chloroformate or a diaryl carbonate or a mixture of an aryl chloroformate and a diaryl carbonate; and
   (c) reacting said polycarbonate or copolycarbonate or aryl chloroformate or diaryl carbonate or mixture of aryl chloroformate and diaryl carbonate in a reactor with additional alkali solution and optionally a chain terminator and optionally a further catalyst;
wherein said continuous mixing in (a) and said reaction in (b) are effected in a pump, wherein said pump
   operates according to the stator-rotor principle and comprises a static housing P, a rotating internal apparatus R comprising blades S, and a circulation channel K;
   is thermostatable to a temperature of from −5° C. to 100° C.; and
   comprises an entrance for said organic phase and an entrance for said aqueous phase and optionally comprises entrances for a catalyst, a chain terminator, a branching agent, and/or additional alkali solution and at least one exit for said polycarbonate or copolycarbonate or aryl chloroformate or diaryl carbonate or mixture of aryl chloroformate and diaryl carbonate.

2. The process of claim 1, wherein a further catalyst is used in (c).

3. The process of claim 1, wherein said pump comprises entrances for additional alkali solution and at least one exit said polycarbonate or copolycarbonate or aryl chloroformate or diaryl carbonate or mixture of aryl chloroformate and diaryl carbonate.

4. The process of claim 1, wherein said pump has one or more rotors.

5. The process of claim 1, wherein said pump is thermostatable to a temperature of from 15° C. to 80° C.

6. The process of claim 5, wherein said pump is thermostatable to a temperature of from 25° C. to 65° C.

7. The process of claim 1, wherein said diphenol is of formula

HO—Z—OH, wherein Z is a divalent organic radical having 6 to 30 carbon atoms and which contains an aromatic group.

8. The process of claim 7, wherein said diphenol is hydroquinone, resorcinol, dihydroxybiphenyls, bis(hydroxyphenyl)alkanes, bis(hydroxyphenyl)cycloalkanes, bis(hydroxyphenyl)sulphides, bis(hydroxyphenyl)ethers, bis(hydroxyphenyl)ketones, bis(hydroxyphenyl)sulphones, bis(hydroxyphenyl)sulphoxides, α,α'-bis(hydroxyphenyl)diisopropylbenzenes, bis(hydroxyphenyl)phthalimidines or the compounds thereof which are alkylated, alkylated on the nucleus, or halogenated on the nucleus.

9. The process of claim 7, wherein said diphenol is 4,4'-dihydroxybiphenyl, 2,2-bis(4-hydroxyphenyl)-1-phenylpropane, 1,1-bis(4-hydroxyphenyl)phenylethane, 2,2-bis(4-hydroxyphenyl)propane (bisphenol A (BPA)), 2,4-bis(4-hydroxyphenyl)-2-methylbutane, 1,3-bis[2-(4-hydroxyphenyl)-2-propyl]benzene (bisphenol M), 2,2-bis(3-methyl-4-hydroxyphenyl)propane, bis(3,5-dimethyl-4-hydroxyphenyl)methane, 2,2-bis-(3,5-dimethyl-4-hydroxyphenyl)propane, bis(3,5-dimethyl-4-hydroxyphenyl)sulphone, 2,4-bis(3,5-dimethyl-4-hydroxyphenyl)-2-methylbutane, 1,3-bis[2-(3,5-dimethyl-4-hydroxyphenyl)-2-propyl]benzene, 2-hydroxycarbyl-3,3-bis(4-hydroxyphenyl)-phthalimidine, 3,3-bis(4-hydroxyphenyl)-1-phenyl-1H-indol-2-one, 2,2-bis(4-hydroxy-phenyl)-1-phenyl-1H-indol-2-one, 3,3-bis(4-hydroxyphenyl)-1-methyl-1H-indol-2-one, 2,2-bis(4-hydroxyphenyl)-1-methyl-1H-indol-2-one, 3,3-bis(4-hydroxyphenyl)-N-methylphthalimidine, 3,3-bis(4-hydroxyphenyl)-N-phenylphthalimidine or 1,1-bis-(4-hydroxyphenyl)-3,3,5-trimethylcyclohexane (bisphenol TMC).

10. The process of claim 1, wherein said monophenol is of formula (I):

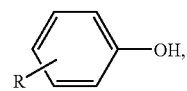

wherein R is hydrogen, halogen, or a branched or straight-chain $C_1$- to $C_9$-alkyl radical or alkoxycarbonyl radical.

11. The process of claim 10, wherein said monophenol is phenol, cresols, p-tert-butylphenol, p-cumylphenol, p-n-octylphenol, p-isooctylphenol, p-n-nonylphenol, p-isononylphenol, p-chlorophenol, 2,4-dichlorophenol, p-bromophenol, 2,4,6-tribromophenol, methyl salicylate, or a mixture thereof.

12. The process of claim 1, wherein said pump in (a) and/or (b) is a centrifugal pump.

13. The process of claim 12, wherein said centrifugal pump is a peripheral wheel pump.

14. The process of claim 1, wherein said pump is designed according to the one-chamber or multichamber principle.

15. A pump for continuously preparing polycarbonate or diaryl carbonate by the phase boundary process, wherein said pump operates according to the stator-rotor principle and comprises a static housing P, a rotating internal apparatus R comprising blades S, and a circulation channel K;

is thermostatable to a temperature of from −5° C. to 100° C.; and comprises at least one entrance for an organic phase and at least one entrance for an aqueous phase.

16. The pump of claim 15, wherein said pump further comprises entrances for a chain terminator, a branching agent, and/or an alkali solution, and a catalyst, and at least one exit for polycarbonate or copolycarbonate or aryl chloroformate or diaryl carbonate or mixture of aryl chloroformate and diaryl carbonate.

17. The pump of claim 16, wherein said pump continually effects (1) the mixing of said organic phase and said aqueous phase, wherein said organic phase comprises a solvent suitable for said polycarbonate or copolycarbonate or diaryl carbonate and phosgene and said aqueous phase comprises a diphenol or a monophenol, water, and alkali solution, and (2) the reaction of said diphenol or said monophenol and phosgene to give a polycarbonate or a copolycarbonate or an aryl chloroformate or a diaryl carbonate or a mixture of aryl chloroformate and diaryl carbonate.

18. The pump of claim 17, wherein said pump is a centrifugal pump.

19. The pump of claim 18, wherein said centrifugal pump is a peripheral wheel pump.

* * * * *